(12) United States Patent
Leu et al.

(10) Patent No.: US 11,078,519 B2
(45) Date of Patent: *Aug. 3, 2021

(54) BIOLUMINESCENT ASSAYS UTILISING SECRETED LUCIFERASES

(71) Applicant: GENE STREAM PTY LTD., City Beach (AU)

(72) Inventors: Marco Peter Leu, East Perth (AU); John Michael Daly, City Beach (AU)

(73) Assignee: GENE STREAM PTY LTD., City Beach (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/439,938

(22) Filed: Jun. 13, 2019

(65) Prior Publication Data
US 2020/0024637 A1 Jan. 23, 2020

Related U.S. Application Data

(60) Continuation of application No. 15/395,047, filed on Dec. 30, 2016, now Pat. No. 10,364,454, which is a
(Continued)

(51) Int. Cl.
*C12Q 1/66* (2006.01)
*C12Q 1/6897* (2018.01)
(Continued)

(52) U.S. Cl.
CPC ............ *C12Q 1/66* (2013.01); *C12N 9/0069* (2013.01); *C12N 9/99* (2013.01); *C12Q 1/6897* (2013.01);
(Continued)

(58) Field of Classification Search
CPC ....................................................... C12Q 1/66
See application file for complete search history.

(56) References Cited

U.S. PATENT DOCUMENTS 5,744,320 A 4/1998 Sherf et al.
5,814,471 A 9/1998 Wood
(Continued)

FOREIGN PATENT DOCUMENTS

JP 2005-245342 9/2005
JP 2008-113620 5/2008
(Continued)

OTHER PUBLICATIONS

Markova et al., "Cloning and expression of cDNA for a luciferase from the marine copepod Metridia longa," J Biol Chem 279(5): 3212-3217, 2004.*
(Continued)

*Primary Examiner* — Rosanne Kosson
(74) *Attorney, Agent, or Firm* — Thompson Hine LLP

(57) ABSTRACT

Disclosed herein are methods for determining the amount or activity of one or more luciferases and methods for measuring the luminescent signal generated by one or more luciferases in a sample, the methods comprising incubating the sample with a reactive substrate(s) of the luciferase(s) to be analysed and a reducing agent to inactivate a first luciferase, wherein the first luciferase, in its native form, is a secreted luciferase.

12 Claims, 19 Drawing Sheets

Related U.S. Application Data division of application No. 14/660,413, filed on Mar. 17, 2015, now Pat. No. 9,567,624, which is a division of application No. 13/795,763, filed on Mar. 12, 2013, now Pat. No. 9,012,164, which is a continuation of application No. 12/519,424, filed as application No. PCT/AU2007/002003 on Dec. 21, 2007, now Pat. No. 8,399,212.

(60) Provisional application No. 60/876,370, filed on Dec. 21, 2006.

(51) Int. Cl.
    *C12N 9/99*     (2006.01)
    *C12N 9/02*     (2006.01)

(52) U.S. Cl.
    CPC ... *C12Y 113/12007* (2013.01); *Y10T 436/182* (2015.01)

(56) References Cited

U.S. PATENT DOCUMENTS

| | | |
|---|---|---|
| 6,171,809 B1 | 1/2001 | Roelant |
| 6,451,549 B1 | 9/2002 | Escher et al. |
| 6,670,449 B1 * | 12/2003 | Miesenbock .... C07K 14/43595 530/350 |
| 6,852,499 B2 | 2/2005 | Ryufuku et al. |
| 2004/0115704 A1 | 6/2004 | Daly |
| 2004/0209274 A2 | 10/2004 | Daly |
| 2004/0224377 A1 | 11/2004 | Hawkins et al. |

FOREIGN PATENT DOCUMENTS

| | | |
|---|---|---|
| WO | 92/04468 | 3/1992 |
| WO | 1996/40988 | 12/1996 |
| WO | 1999/38999 | 8/1999 |
| WO | 00/18953 | 4/2000 |
| WO | 2003/044223 | 5/2003 |
| WO | 2006/085972 | 8/2006 |
| WO | 2006/096735 | 9/2006 |
| WO | 2006/121331 | 11/2006 |
| WO | 2006/130551 | 12/2006 |
| WO | 2008/049160 | 5/2008 |

OTHER PUBLICATIONS

Extended European Search Report 14195943.7 dated Jan. 26, 2015 (6 pages).
International Search Report PCT/AU2007/002003 dated Mar. 3, 2008 (4 pages).
Osamu S. et al, Isolation and properties of the luciferase stored in the ovary of the Scyphozoan Medusa Periphyll periphylla, Biol Bull. (Dec. 2001) vol. 201 p. 339-347.
Written Opinion of the International Search Authority PCT/AU2007/002003 dated Jan. 18, 2008 (5 pages).
International Preliminary Report on Patentability PCT/AU2007/002003 dated Jun. 24, 2009 (1 page).
Shimomura et al. Isolation and Properties of the Luciferase Stored in the Ovary of the Scyphozoan Medusa *Periphylla periphylla*. Biol. Bull. vol. 201 (2001), pp. 339-347.
International Search Report for PCT/AU2007/002003, dated Mar. 3, 2008.
International Search Report and Written Opinion PCT/AU2007/002003, dated Mar. 3, 2008 (9 pages).
International Preliminary Report on Patentability PCT/AU2007/002003, dated Jun. 24, 2009 (6 pages).
Markova et al. Cloning and Expression of cDNA for a Luciferase from the Marine Copepod *Metridia longa*. J. Biol. Chem. vol. 279, No. 5 (2004) pp. 3212-3217.
Supplementary European Search Report EP07845439.4, dated Jan. 20, 2010 (5 pages).
Communication, EP07845439.4, dated Jun. 19, 2013 (4 pages).
Patent Examination Report No. 1, AU2007335194, dated Nov. 8, 2012 (3 pages).
Notice of Rejection, English Summary JP2009-541700 dated Mar. 19, 2013 (8 pages).
Notification of Defects, English Translation IL199456 dated Aug. 15, 2011 (2 pages).
Rodionova and Petushkov. Effect of different salts and detergents on luciferin—luciferase luminescence of the enchytraeid *Fridericia heliota* , J. Photochemistry and Photobiology B: Biology, vol. 83, No. 2 (2006), pp. 123-128.
Gerasimova and Kudryasheva. Effects of potassium halides on bacterial bioluminescence, J. Photochemistry and Photobiology B: Biology vol. 66, No. 3 (2002), pp. 218-222.

\* cited by examiner

BIOLUMINESCENT ASSAYS UTILISING SECRETED LUCIFERASES

RELATED APPLICATION

This application is a continuation of a co-pending U.S. application Ser. No. 15/395,047 filed Dec. 30, 2016, which is a divisional of U.S. application Ser. No. 14/660,413 filed Mar. 17, 2015, now U.S. Pat. No. 9,567,624, which is a divisional of U.S. application Ser. No. 13/795,763, filed Mar. 12, 2013, now U.S. Pat. No. 9,012,164, which is a continuation of U.S. application Ser. No. 12/519,424 filed Nov. 2, 2009, now U.S. Pat. No. 8,399,212, which is a National Stage of International application Serial No. PCT/AU2007/002003 filed Dec. 21, 2007 which claims priority to U.S. application Ser. No. 60/876,370 filed Dec. 21, 2006, each of which is expressly incorporated by reference in its entirety.

FIELD OF THE INVENTION

The present invention relates generally to reagents and compositions for use in reactions catalysed by luciferase enzymes, and in particular for use in luciferase-based reporter gene assays. The invention also provides methods and compositions for, inter alia, increasing the sensitivity and/or improving the kinetics of luciferase-catalysed reactions.

BACKGROUND OF THE INVENTION

Reporter gene assays represent an important tool in studies of gene expression, permitting an understanding of what controls the expression of a gene of interest e.g., DNA sequences, transcription factors, RNA sequences, RNA-binding proteins, signal transduction pathways and specific stimuli. In particular, reporter assays can be used to identify nucleic acid regions important in gene regulation. Such regions may serve as potential targets for therapeutic intervention in the treatment or prevention of human diseases. Reporter assays can also be used to screen drugs for their ability to modify gene expression.

Typically reporter assays are used to identify a gene promoter region or specific elements within a promoter, such as transcription factor binding sites or other regulatory elements. Alternatively, such assays are used to study the response to various stimuli or agents of a promoter or regulatory element. In some applications, the reporter constructs used in the assay, or transfected cells, are introduced into an organism to study promoter function in vivo. Further, reporter assays can be used to study or measure signal transduction pathways upstream of a specific promoter.

By way of example, in the case of reporter assays designed to investigate putative promoter sequences or other transcriptional regulatory elements, nucleic acids to be interrogated are cloned into reporter plasmids in a location so as to permit the regulation of transcription of a downstream reporter gene, and thus expression of a reporter protein encoded by the reporter gene. The reporter protein should be distinguishable from endogenous proteins present in the cell in which the reporter plasmid is transfected for ease of detection, and preferably expression of the reporter protein should be readily quantifiable. The reporter protein is quantified in an appropriate assay and often expressed relative to the level of a control reporter driven by a ubiquitous promoter such as for example the promoter SV40. The control reporter must be distinguishable from the test reporter and is generally contained on a separate vector that is co-transfected with the test vector and used to control for transfection efficiency. Such assays are based on the premise that cells take up proportionally equal amounts of both vectors.

A variety of different applications for reporter gene assays involve measuring a change in gene expression over time or after addition of a compound, drug, ligand, hormone etc. This is of particular importance in drug screening. Following the addition of the drug, detecting a measurable change in levels of the reporter protein may be delayed and diluted as changes in expression levels are transmitted through mRNA to protein. A significant advance in such applications recently made by the present Applicant is the combined use of mRNA- and protein-destabilizing elements in the reporter vector to improve the speed and magnitude of response, as described in co-pending U.S. patent application Ser. No. 10/658,093, the disclosure of which is incorporated herein by reference.

Various reporter gene assay systems are commercially available utilising different detectable reporter proteins, the most common being chloramphenicol transferase (CAT), β galactosidase (β-gal), fluorescent proteins and luciferases.

Luciferase is the most commonly used reporter protein for in vitro assay systems. Luciferases are enzymes capable of bioluminescence and are found naturally in a range of organisms. In commercially available assay systems, luciferases are typically divided into those which utilise luciferin as a substrate and those which utilise coelenterazine as a substrate. The most widely employed example of the former is firefly luciferase, an intracellular enzyme. Additional examples of luciferases utilising luciferin include those derived from other members of *Coleoptera*, such as click beetles and railroad worms, and *Diptera* (as disclosed, for example, in WO 2007/019634). Luciferases utilising coelenterazine are typically derived from marine organisms such as the soft coral *Renilla* or the copepod *Gaussia*. *Renilla* luciferase is intracellular, whereas *Gaussia* luciferase in its native state is a secreted enzyme. Other secreted luciferases include those from *Metridia longa*, *Vargula hilgendorfii*, *Oplophorus gracilirostris*, *Pleuromamma xiphias* and other members of Metridinidae.

Luciferase-based assay systems may employ more than one luciferase, typically of different origin and each utilising a different substrate, enabling both test and control reporter to be measured in the same assay. The ability to measure the signals emitted by multiple luciferases in a single sample provides obvious benefits, including the ability to measure multiple parameters in a single experiment. Typically, two different reporter genes, differing in both the type of luciferase encoded and the regulatory element of interest controlling expression of each luciferase are inserted into a single cell line.

By way of example, a putative promoter element is cloned upstream of a firefly luciferase reporter gene such that it drives its expression. This plasmid is transiently transfected into a cell line, along with a control plasmid containing the *Renilla* luciferase gene driven by the SV40 promoter. First luciferin is added to activate the firefly luciferase, activity of this reporter is measured, and then a "quench and activate" reagent is added. This reagent contains a compound that "quenches" the luciferin signal and also contains coelenterazine to activate the *Renilla* luciferase, the activity of which is then measured. The Promega Dual-Glo Luciferase Assay is one example of such a system.

The level of firefly luciferase activity is dependent, not only on promoter activity, but also on transfection efficiency.

This varies greatly, depending on the amount of DNA, the quality of the DNA preparation and the condition of the cells. The co-transfected control plasmid (*Renilla* luciferase driven by a suitable promoter such as the SV40 promoter) is used to correct for these variables, based on the premise that *Renilla* luciferase activity is proportional to the amount of firefly luciferase plasmid taken up by the cells. Alternatively or additionally, the *Renilla* luciferase may be used to control for other variables, such as cell number, cell viability and/or general transcriptional activity; or may be used to determine whether a particular treatment or compound applied to the cells affects both promoters or is specific to one of them.

An alternative method for distinguishing the signals of two or more luciferases in a single sample is exemplified by TOYO B-net's Multicolor-Luc Assay, which utilizes three different beetle luciferases that act on the same substrate (luciferin) but which emit light at different wavelengths. However, in this case optical filters are required to separate the different signals and this leads to a reduced quantifiable signal per luciferase.

It is desirable to employ a dual-luciferase assay system that allows the test element (e.g. promoter) to be linked to a highly sensitive luciferase system, such that it provides sufficient signal intensity over a wide range of different applications, including the use of weak promoters or difficult to transfect cells. Signal strength is far less important for the control reporter because; a) the control is not essential to the experiment and; b) a strong control promoter, such as SV40, RSV, EF1alpha or CMV can be selectively chosen to ensure that sufficient signal is generated. In other words, a luciferase that generates only a weak signal (per molecule of luciferase protein or luciferase gene) can be selectively combined with a strong control promoter to ensure that a detectable signal is generated. Users do not have this flexibility in terms of choosing test promoters.

In this context the commercially available Dual-Glo Luciferase Assay (Promega) has the disadvantage of utilizing the more sensitive *Renilla* luciferase for the control reporter and the less sensitive firefly luciferase for the test reporter. Further, the system requires that firefly signal is measured first.

The commercially available Multicolor-Luc Assay system (TOYO B-net) utilizes three beetle luciferases that have even lower sensitivity than firefly luciferase. Furthermore, it is not possible to measure an individual luciferase without the use of filters, which results in a further loss of sensitivity. Additionally, most commonly used luminometers are not compatible with protocols requiring discrimination of multiple wavelengths.

Luciferase-based assay systems, in particular those utilising one or more intracellular luciferases, typically employ two buffers, a lysis buffer and an assay buffer. The lysis buffer is added to the cells first to lyse the cells and thus release luciferase, facilitating subsequent measurement. An assay buffer containing the luciferase substrate and any cofactors is then added, after which, a measurement of luciferase activity is taken. Measurement may be made immediately (i.e. within seconds) of the addition of the assay buffer (so-called "flash" reaction), or minutes or hours later (so-called "glow" reactions) by using "glow" reagents in the assay buffer that keep the light signal stable for an extended period of time. Flash reactions provide the highest signal strength (light units per second) and thereby have the advantage of providing highest sensitivity. Glow reactions are particularly advantageous in applications where, for example, the user does not have a suitable luminometer (equipped with injectors) readily available or in some high throughput screening applications where batch-processing requires a delay between injection and measurement. Glow reagents for *Coleoptera* luciferases can be produced by including a thiol such as CoA or DTT in the reagent composition (see, for example, U.S. Pat. Nos. 5,650,289 and 5,641,641). DTT has also been shown to extend the glow of *Renilla* luciferases (U.S. Pat. No. 6,171,809).

There are a number of disadvantages associated with existing buffers and reagents for luciferase reporter assays.

In particular, there is a need for reagents, reaction compositions and kits, including multi-luciferase systems that provide improved sensitivity in luciferase reactions; that is, a signal strength of greater intensity than is achievable with existing reagents. This is of particular relevance where the reporter gene assayed provides only low levels of luciferase in the cells of interest, for example, where the promoter being studied has only low activity, and/or where the cells of interest are difficult to transfect/transduce with the reporter vector. Increased sensitivity would also facilitate the miniaturization of reporter assays by reducing the minimum number of cells required to yield a signal strength that can be reliably measured.

When utilizing assay systems including destabilizing elements such as those described in co-pending U.S. patent application Ser. No. 10/658,093, the steady-state luciferase signal is reduced. Thus, reagents that provide higher signal strength would be particularly advantageous for reporter assay systems utilizing destabilizing elements.

Also in the context of improving the signal strength or sensitivity of a luciferase signal, an assay reagent with reduced background luminescence would improve performance by increasing the signal to noise ratio, providing the reduction in background is not associated with a reduction in the true luciferase signal.

Existing methods for quantifying bioluminescence in multi-well plates tend to suffer from the problem of light leakage between wells. A signal that decays rapidly would minimize this unwanted artefact whilst also enabling the subsequent measurement of additional parameters that utilize light emission or fluorescence as a read-out. With current luciferase assay systems some level of light emission persists long after measurement, even with the use of so-called 'flash' reagents. This signal serves no useful purpose as the intent of flash reactions is to measure light emission immediately after injection of assay buffer. Moreover, the persisting signal can interfere with subsequent measurements of luminescence or fluorescence. In some contexts a quenching reagent could be added to terminate the luciferase signal. However, a self-terminating signal that does not require this additional pippetting step would provide a simpler and more preferable system.

A further limitation of current luciferase assays is the number of different luciferases that can be distinguished and measured in a single sample. As described above, quenching reagents and differences in emission wavelength have been utilized to separate signals generated by two or three different luciferases. An additional means of separating the signal from different luciferases would enable assay systems capable of measuring four or more different luciferases and therefore enable the analysis of four or more different parameters in the same sample. To enable simultaneous measurement of multiple different luciferases, it is necessary to have a reagent system capable of supporting the activity of the different luciferases. Further, to enable sequential activation and measurement of multiple different luciferases, it is necessary to have a reagent system that allows termination of the first luciferase reaction without impeding subsequent luciferase reactions.

SUMMARY OF THE INVENTION

The present invention relates generally to methods for use in determining the amount or activity of a luciferase enzyme in a sample. The present invention is predicated, in part, on the inventors' surprising finding that thiols and reducing agents such as DTT markedly shorten the period of luminescence generated from luciferases that are secreted in their native form. Additionally, the inventors have surprisingly determined that inactivation of such naturally secreted luciferases by reducing agents is time-dependent. The delay in inactivation provides a window of opportunity for measuring luminescence (for example in flash reactions) prior to loss of luminescent signal. Thus, embodiments of the invention enable the generation of higher sensitivity (stronger flash phase and/or lower background signal) and a faster rate of luminescent signal decay for secreted luciferases than is currently achievable using available luciferase assay methodologies and reagent compositions.

The invention therefore also offers novel approaches to measuring luminescence in multi-luciferase (e.g. dual and triple luciferase) assays. Such methods have applications primarily in gene reporter assays. However, utility in other areas is also apparent. For example, luciferases can be used to label antibodies (e.g. for immunocytochemistry) or to label proteins (e.g. for BRET assays). The ability to experimentally and selectively switch on and/or off certain luciferases enables multiple different luciferase labels to be used in a single sample. In the case of BRET assays, blue light emitting luciferases are preferred and are used to activate fluorescence from a fluorescent protein in close proximity. The present invention provides a means to distinguish or manipulate luminescence from two different blue emitting luciferases, thereby facilitating multi-BRET assays.

A first aspect of the invention provides a method for measuring the luminescent signal generated by one or more luciferases in a sample, the method comprising incubating the sample with a reactive substrate(s) of the luciferase(s) to be analysed and a reducing agent to inactivate a first luciferase, wherein the first luciferase, in its native form, is a secreted luciferase.

The inactivation of the first luciferase may comprise inhibiting or abolishing the catalytic activity of the luciferase and/or converting the luciferase into an inactive conformation.

The first luciferase may be a non-secreted modified form of a luciferase that is secreted in its native form. The first luciferase may utilise coelenterazine as a substrate. The first luciferase may utilise coelenterazine as a substrate and be of marine origin. The luciferase of marine origin may be derived from *Gaussia* spp., *Pleuromamma* spp., *Metridia* spp., *Cypridina* spp., or *Oplophorus* spp., or is a variant or derivative thereof.

The reducing agent may comprise a thiol group. The reducing agent may be selected from the group consisting of dithiothreitol (DTT), dithioerythreitol (DTE), β-mercaptoethanol, cysteamine, sodium sulphite and tris(2-carboxyethyl)phosphine (TCEP). The reducing agent may be DTT.

In an embodiment, the luminescent signal generated by the first luciferase is measured. In such embodiments, (i) the reactive substrate of the first luciferase may be added simultaneously with the reducing agent, (ii) the reactive substrate of the first luciferase may be added to the sample and the luminescent signal generated by the first luciferase is measured prior to addition of the reducing agent, or (iii) the reducing agent may be added to the sample prior to the reactive substrate of the first luciferase and the luminescent signal generated by the first luciferase is measured before the first luciferase is inactivated by the reducing agent.

In an embodiment, at least one of the luciferases is expressed from a recombinant reporter gene. The luminescent signal may be measured as part of a reporter gene assay.

The sample may comprise at least one intracellular luciferase. In an embodiment the intracellular luciferase may be derived from a *Coleoptera* or a *Diptera* species.

Where the sample comprises at least one intracellular luciferase, the reducing agent may added to the sample prior to addition of the reactive substrate of the intracellular luciferase such that the first luciferase is inactivated prior to measurement of the luminescent signal generated by the intracellular luciferase. The intracellular luciferase may be activated by the reducing agent. The period of light emission from the intracellular luciferase may be extended by the reducing agent. The first and second luciferases may utilise the same or different substrates. For example, the first luciferase may utilise coelenterazine as a substrate and the intracellular luciferase may utilise luciferin as a substrate, or both the first luciferase and the intracellular luciferase may both utilise coelenterazine as a substrate.

The sample may comprise two or more intracellular luciferases. The luminescent signals generated by the two or more intracellular luciferases may be produced at different wavelengths.

A second aspect of the invention provides a method for measuring the luminescent signal generated by a luciferase in a sample, wherein the luciferase, in its native form, is a secreted luciferase, the method comprising:

(a) contacting the sample with a reactive substrate of the luciferase;

(b) contacting the sample with a reducing agent that time dependently inactivates the luciferase; and (c) measuring the luminescent signal generated by the luciferase before the luciferase is inactivated by the reducing agent.

The luciferase may be a non-secreted modified form of a luciferase that is secreted in its native form.

The sample may be contacted with the reactive substrate prior to the reducing agent or contacted simultaneously with the reactive substrate and the reducing agent.

A third aspect of the invention provides a method for measuring the luminescent signal generated by a luciferase in a sample, wherein the luciferase, in its native form, is a secreted luciferase, the method comprising:

(a) contacting the sample with a reactive substrate of the luciferase;

(b) measuring the luminescent signal generated by the luciferase; and (c) subsequently contacting the sample with a reducing agent that time dependently inactivates the luciferase.

A fourth aspect of the invention provides a method for measuring the luminescent signal generated by a luciferase in a sample, wherein the luciferase, in its native form, is a secreted luciferase, the method comprising:

(a) contacting the sample with a reducing agent that time dependently inactivates the luciferase;

(b) contacting the sample with a reactive substrate of the luciferase; and (c) measuring the luminescent signal generated by the luciferase before the luciferase is inactivated by the reducing agent.

A fifth aspect of the invention provides a method for measuring the luminescent signal generated by a first and second luciferase in a sample, wherein the first luciferase, in its native form, is a secreted luciferase and the second luciferase is an intracellular luciferase, the method comprising:

(a) contacting the sample with a reactive substrate of the first luciferase;

(b) measuring the luminescent signal generated by the first luciferase;

(c) contacting the sample with a reducing agent that time dependently inactivates the first luciferase;

(d) contacting the sample with a reactive substrate of the second luciferase; and (e) measuring the luminescent signal generated by the second luciferase.

Steps (d) and (e) may precede steps (a) through (c) such that the luminescent signal generated by the second luciferase is measured prior to measurement of the luminescent signal generated by the first luciferase.

Step (b) may be carried out after steps (a) and (c), such that the sample is contacted with the reducing agent prior to measurement of the luminescent signal generated by the first luciferase.

The sample may be contacted with the reducing agent prior to, or simultaneously with, the reactive substrate of the first luciferase.

A sixth aspect of the invention provides a method for measuring the luminescent signal generated by a second luciferase in a sample comprising a first and second luciferase, wherein the first luciferase, in its native form, is a secreted luciferase, and the second luciferase is an intracellular luciferase, the method comprising the steps of:

(a) contacting the sample with a reducing agent that time dependently inactivates the first luciferase;

(b) contacting the sample with a reactive substrate of the second luciferase; and (c) measuring the luminescent signal generated by the second luciferase.

The sample may further comprise a third luciferase. The third luciferase may be an intracellular luciferase. The luminescent signals generated by the second and third luciferases may be produced at different wavelengths. The second luciferase may be derived from a *Coleoptera* species and the third luciferase derived from a *Diptera* species.

A seventh aspect of the invention provides a method for inactivating a luciferase that, in its native form, is a secreted luciferase, the method comprising contacting a sample containing the luciferase with a reducing agent.

The luciferase may be a non-secreted modified form of a luciferase that is secreted in its native form.

The inactivation of the luciferase may comprise inhibiting or abolishing the catalytic activity of the luciferase and/or converting the luciferase into an inactive conformation.

An eighth aspect of the invention provides a method for increasing the rate of decay of the luminescent signal generated by a luciferase that, in its native form, is a secreted luciferase, the method comprising contacting a sample containing the luciferase with a reducing agent.

A ninth aspect of the invention provides a method for measuring the luminescent signal generated by one or more luciferases in a sample, the method comprising incubating the sample with a reactive substrate(s) of the luciferase(s) to be analysed and a reagent composition that provides an environment suitable to facilitate conversion of a first luciferase into an inactive conformation, wherein the first luciferase is, in its native form, a secreted luciferase.

A tenth aspect of the invention provides a method for determining the amount or activity of two or more luciferases in a sample, the method comprising:

(a) adding to the sample an effective amount of a reducing agent that time dependently inactivates the first luciferase;

(b) measuring the luminescent signal in the sample;

(c) waiting for a period of time to allow the luminescent signal of the first luciferase to decline;

(d) measuring the luminescent signal in the sample; and (e) calculating the luminescent signal of each luciferase based on the results of (b) and (d) and the differing rates of decay in each luminescent signal.

An eleventh aspect of the invention provides a method for determining the amount or activity of a first and second luciferase in a sample, the method comprising (a) contacting the sample with reactive substrates for the first and second luciferases and a reducing agent that time dependently inactivates the first luciferase but does not inactivate the second luciferase;

(b) measuring the luminescent signal before the first luciferase is inactivated by the reducing agent;

(c) measuring the luminescent signal after the first luciferase is inactivated; and (d) using the data collected in (b) and (c) to calculate the amounts or activities of each luciferase relative to each other or relative to other samples.

A twelfth aspect of the invention provides a method for determining the amount or activity of a first and second luciferase in a sample, the method comprising (a) contacting the sample with a reactive substrate for the first luciferase and a reducing agent that time dependently inactivates the first luciferase but does not inactivate the second luciferase;

(b) measuring the luminescent signal before the first luciferase is inactivated;

(c) contacting the sample with a reactive substrate for the second luciferase;

(d) measuring the luminescent signal after the first luciferase is inactivated; and (e) using the data collected in (b) and (c) to calculate the amounts or activities of each luciferase relative to each other or relative to other samples.

A thirteenth aspect of the invention provides a method for determining the amount or activity of one or more luciferases in a sample, the method comprising incubating the sample with a reactive substrate(s) of the luciferase(s) to be analysed and a reducing agent to inactivate a first luciferase, wherein the first luciferase, in its native form, is a secreted luciferase.

According to aspects and embodiments of the invention the sample may be subjected to a cell lysis step prior to measurement of luminescent signal. The sample may be subjected to a cell lysis step prior to addition of the luciferase substrate(s). The sample may be subjected to a cell lysis step prior to addition of the reducing agent. The reducing agent may be present in cell lysis buffer.

According to aspects and embodiments of the invention the luminescent signal may be measured using conditioned medium in which the cells expressing a luciferase(s) have been cultured.

Also disclosed herein is a reagent composition for use in determining the amount or activity of luciferase in a sample, wherein the reagent composition permits generation of an enhanced luminescent signal and/or an increased rate of luminescent signal decay from the luciferase. Typically, in the presence of the luciferase, the reagent composition provides an environment suitable to facilitate conversion of the luciferase into an inactive conformation. Typically the conversion occurs in a timeframe such that the luminescent signal can be measured prior to said conversion. Typically the conversion becomes evident at about 1 or more seconds, about 5 or more seconds or about 10 or more seconds after the initiation of the luminescent signal. Typically the conversion is progressive over time.

Also disclosed herein is a reagent composition for use in determining the amount and/or activity of luciferase in a sample, wherein in the presence of the luciferase, the reagent composition provides a redox environment suitable to facilitate conversion of the luciferase into an inactive conformation. Typically the environment provided by the reagent composition facilitates a more rapid conversion of active luciferase to an inactive conformation or adoption or maintenance of a less active conformation. Alternatively or additionally, the environment may decrease the overall activity of luciferase in a sample by increasing the proportion of luciferase that adopts the inactive conformation. Typically, the reagent composition comprises at least one suitable reducing agent. Typically the agent(s) results in reduction of the luciferase thereby facilitating the adoption, in a time dependent manner, of an inactive conformation by the luciferase. Accordingly, the ratio of signal intensity in the presence of the agent versus in the absence of the agent (+agent/−agent) typically decreases over time. For example, the ratio is typically lower at 10 minutes than at 1 second after contacting the reagent composition with the luciferase.

Also disclosed herein is a kit for use in assaying the amount and/or activity of one or more luciferases, the kit comprising at least one reagent composition wherein the reagent composition provides an environment suitable to facilitate conversion of at least one of the luciferases into an inactive conformation.

Also disclosed herein is a kit for use in assaying the amount and/or activity of one or more luciferases, the kit comprising at least one reagent composition wherein the reagent composition provides a redox environment suitable to promote unfolding of at least one of the luciferases into an inactive conformation.

Also disclosed herein is a reagent composition for use in determining the amount or activity of luciferase in a sample, the reagent composition comprising at least one reducing agent.

Also disclosed herein is a reagent composition for use in determining the amount or activity of luciferase in a sample, the reagent composition comprising at least one reducing agent or combination of oxidising and reducing agents. Typically the agent(s) result in the reduction of the luciferase thereby facilitating the adoption of an inactive conformation by the luciferase.

In accordance with the above, the reagent composition may further comprise one or more additional components. Such additional components may be selected from, for example, divalent metal chelators, antioxidants, protease inhibitors, salts. detergents, or additional buffer components. The divalent metal chelator may, for example, be selected from EDTA, CDTA and EGTA. In one embodiment, the divalent metal chelator is EDTA, present at a concentration of between about 1 mM and about 15 mM. The reagent composition may be in the form of an assay reagent or buffer for use in measuring the activity of the luciferase. Accordingly, the assay buffer may further comprise additional components such as a buffering agent. The buffering agent may, for example, be Tris, Hepes or a phosphate buffer. The reagent composition may further comprise a luciferase substrate. The substrate may, for example, be luciferin or coelenterazine. In a particular embodiment the substrate is coelenterazine or a derivative thereof. By way of example, the coelenterazine or derivative thereof may be present in a concentration of more than about 2 uM, more than about 5 uM, more than about 10 uM, more than about 15 uM, more than about 20 uM or more than about 25 uM.

Typically the bioluminescent signal generated by the luciferase is short-lived and declines to near background levels within about 15 minutes after addition of substrate. More typically the signal declines to less than about 1% of the initial signal within about 15 minutes after addition of substrate, within about 10 minutes after the addition of substrate, or within about 5 minutes after the addition of substrate. Typically the bioluminescent signal declines rapidly from within a few seconds after addition of substrate, to a level that is less than about 0.1% of the initial signal within about 60 minutes after addition of substrate, within about 30 minutes after addition of substrate, within about 15 minutes after addition of substrate, within about 10 minutes after the addition of substrate, or within about 5 minutes after the addition of substrate.

Also disclosed herein is a reagent composition for use in determining the amount or activity of luciferase in a sample, wherein the reagent composition comprises DTT and coelenterazine, wherein the luciferase utilises coelenterazine as a substrate.

Also disclosed herein is a method for determining the amount or activity of luciferase in a sample, the method comprising: (a) adding to the sample an effective amount of a reagent composition according to any one of the first, second, fifth, sixth or seventh aspects; and (b) detecting bioluminescence in the sample.

Also disclosed herein is a method for reducing the background signal or increasing the signal:noise ratio of a luciferase reaction, the method comprising contacting the luciferase with an effective amount of a reagent composition that comprises a substrate for the luciferase plus a suitable redox environment. Typically, the reagent composition comprises at least one reducing agent or combination of oxidising and reducing agents.

Also disclosed herein is a method of increasing the rate of decay of the bioluminescent signal generated by a luciferase enzyme, the method comprising contacting the luciferase with an effective amount of a reagent composition, wherein the reagent composition provides a redox environment suitable to facilitate conversion of the luciferase into an inactive conformation.

Also disclosed herein is a method for determining the amount or activity of luciferase in a sample, the method comprising: (a) providing cells expressing luciferase; (b) adding a reagent composition comprising a substrate of the luciferase enzyme and suitable for facilitating conversion of the luciferase into an inactive state or conformation; and (c) detecting the bioluminescent signal generated by the active luciferase.

Also disclosed herein is a method for determining the amount or activity two luciferases in a sample, the method comprising:

(a) determining the amount or activity of a first luciferase in accordance with the eighth or tenth aspect; (b) waiting for a period of time to allow the luminescent signal of the first luciferase to substantially decline; (c) adding a second substrate for the second luciferase; and (d) measuring the luminescent signal generated by the second luciferase.

The above method is also applicable to the determination of the amount or activity of more than two luciferases in a sample, the method comprising the repetition of steps (c) and (d) or step (d) alone for each additional luciferase.

Also disclosed herein is a method for determining the amount or activity of two luciferases in a sample, the method comprising: (a) adding to the sample an effective amount of reagent composition, the composition being suitable for generating a luminescent signal from the two luciferases but with a different rate of decay of the luminescent signal for each luciferase; (b) measuring the luminescent signal in the sample; (c) waiting for a period of time to allow the luminescent signal of the first luciferase to decline; (d) measuring the luminescent signal in the sample; and (e) calculating the luminescent signal of each luciferase based on the results of (b) and (d) and the differing rates of decay in each luminescent signal.

Also disclosed herein is a method for determining the amount or activity of a luciferase in a sample, the method comprising (a) contacting the sample with a reagent composition that comprises both a reactive substrate of the luciferase and an agent that time dependently reduces or inactivates the catalytic activity of the luciferase; and (b) measuring the luminescent signal before the catalytic activity of the luciferase is reduced or inactivated by the agent.

Also disclosed herein is a method for determining the amount or activity of a first and second luciferase in a sample, the method comprising (a) contacting the sample with a first reagent composition that comprises a substrate for the first and second luciferases and an agent that time dependently reduces or inactivates the catalytic activity of the first luciferase but does not reduce or inactivate the catalytic activity of the second luciferase; (b) measuring the luminescent signal before the catalytic activity of the first luciferase is reduced or inactivated by the agent; (c) measuring the luminescent signal after the catalytic activity of the first luciferase is reduced or inactivated by the agent; and (d) using the data collected in (b) and (c) to calculate the amounts or activities of each luciferase relative to each other or relative to other samples.

Also disclosed herein is a method for determining the amount or activity of a first and second luciferase in a sample, the method comprising (a) contacting the sample with a first reagent composition that comprises a substrate for the first luciferase and an agent that time dependently reduces or inactivates the catalytic activity of the first luciferase but does not reduce or inactivate the catalytic activity of the second luciferase; (b) measuring the luminescent signal before the catalytic activity of the first luciferase is reduced or inactivated by the agent; (c) contacting the sample with a second reagent composition that comprises a substrate for the second luciferase; (d) measuring the luminescent signal after the catalytic activity of the first luciferase is reduced or inactivated by the agent; and (e) using the data collected in (b) and (c) to calculate the amounts or activities of each luciferase relative to each other or relative to other samples.

BRIEF DESCRIPTION OF THE DRAWINGS

Embodiments of the present invention will now be described, by way of example only, with reference to the accompanying drawings.

FIGS. 11A and 11B show data from a single time point without doxycycline treatment and FIGS. 11C and 11D show the data from all time points expressed as +doxycycline relative to −doxycycline.

DETAILED DESCRIPTION OF THE INVENTION

Figure 1A:
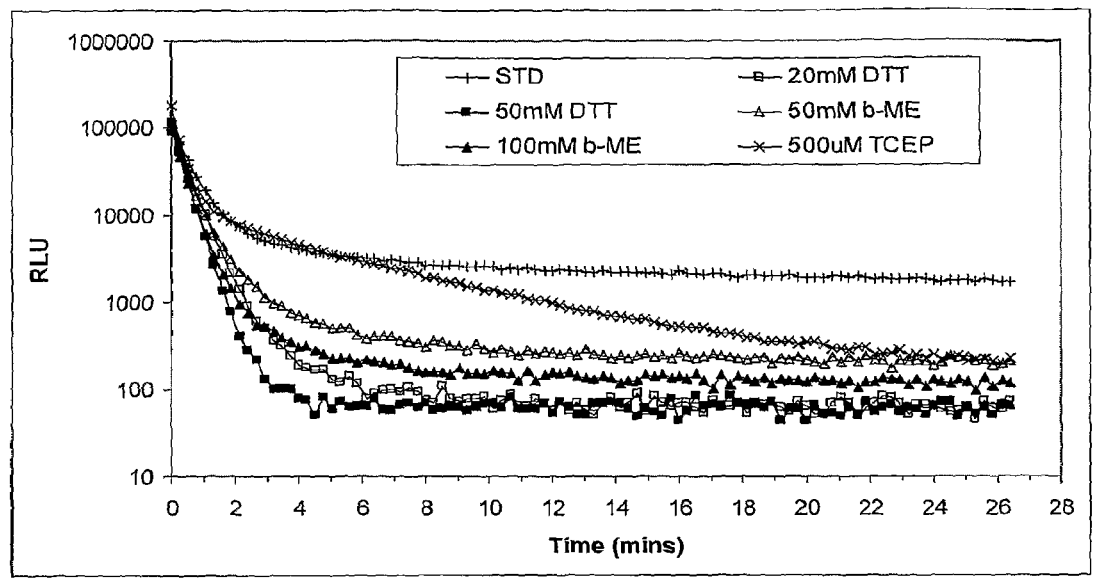
FIGS. 1A-B show the kinetics of bioluminescence in relative light units (RLU) over time for a non-secreted *Gaussia* luciferase in the presence of varying concentrations of three different reducing agents.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

As used herein in the context of the conversion of a luciferase enzyme from one conformation to another, the term "facilitates" means that an agent enables, produces, permits or promotes such conversion. Thus, facilitation of the conversion of luciferase into an inactive conformation may be passive or active, and direct or indirect. For example, the agent may provide a suitable environment in which conversion of the luciferase into an inactive conformation may take place. Alternatively, the agent may directly or indirectly promote or otherwise produce or generate such a conversion. An agent that "facilitates" conversion of a luciferase enzyme is typically one that provides for a more efficient conversion relative to that observed in the absence of the agent.

As used herein, the term "conversion" refers to the folding/unfolding or other modification of a luciferase enzyme in achieving an active/inactive state or conformation. Further reference to conversion of a luciferase into an inactive conformation is to be taken to mean either the conversion from an active state or conformation to an inactive state or conformation, or the conversion from a partially active or more active state or conformation to a less active state or conformation. In this context the term "conformation" includes within its scope the structure (for example tertiary or quaternary) adopted by the enzyme and which correlates with the ability of the enzyme to catalyse a reaction and thereby generate a bioluminescent signal upon addition of substrate.

The term "enhanced" as used herein in the context of the bioluminescent signal intensity of a luciferase means enhanced or increased, qualitatively or quantitatively, signal intensity or signal:noise ratio relative to that achieved in the absence of an agent or reagent composition and/or in the presence of a composition of the prior art. Similarly, the term "increased rate of decay" is used to indicate a rate of decay of bioluminescent signal that is increased relative to that achieved in the absence of the agent or reagent composition and/or in the presence of a composition of the prior art.

As used herein the term "effective amount" includes within its meaning a sufficient amount of a reagent composition to provide the desired effect. The exact amount required will vary from case to case depending on factors such as the nature of the sample to be analyzed, the luciferase enzyme used and whether the luciferase is intracellular or secreted, and the constitution of the reagent or composition used. Thus, it is not possible to specify an exact "effective amount". However, for any given case, an appropriate "effective amount" may be determined by one of ordinary skill in the art using only routine experimentation.

As used herein the term "non-secreted luciferase" means a luciferase that is not exported or secreted from a cell into the extracellular environment. Thus "non-secreted" includes a luciferase retained in the cell in any form, and thus the luciferase may be cytoplasmic or membrane-associated. Typically, although not exclusively, where a luciferase is referred to herein as being a "non-secreted" form of a luciferase that is secreted in its native form, this secretion and absence of secretion refers to eukaryotic cells.

As used herein the term "secreted luciferase" refers to a luciferase that, in its native form, is secreted from the cell in which it is normally expressed into an extracellular location. The extracellular location may be internal or external to the organism depending on the identity of the organism. The extracellular location includes within its scope the medium in which a cell expressing the luciferase is being cultured in vitro. It may also include the aquatic or marine environment in which the organism that expresses the luciferase usually resides. It should also be noted that encompassed by the term "secreted luciferase" are various modified and recombinant forms thereof as described herein, wherein such recombinant or modified forms may or may not be secreted. Thus, the term "secreted luciferase" includes within its scope "non-secreted" forms of secreted luciferases.

As used herein the term "intracellular luciferase" refers to a luciferase that upon expression, and in its native form, is retained within the cell or cell membrane rather than secreted into the extracellular medium. It should be noted that encompassed by the term "intracellular luciferase" are various modified and recombinant forms thereof as described herein, wherein such recombinant or modified forms may or may not remain intracellular. Thus, the term "intracellular luciferase" includes within its scope exported or secreted forms of intracellular luciferases.

Thus, as used herein the terms "non-secreted" and "intracellular" have distinct meanings. A "non-secreted" luciferase may be one that is a modified form of a luciferase that is secreted in its native form, whereas an "intracellular" luciferase is one that is intracellular (not secreted) in its native form.

As used herein the terms "inactivate", "inactivation" and variations thereof as used herein mean, in the context of inactivation of a luciferase by a reducing agent, that the catalytic activity of the luciferase as determined by the amount of luminescent signal generated is reduced or abolished. Thus, inactivation may be complete in that 100% reduction in activity may result, but this need not be the case. Partial inactivation such that some residual activity is retained is also contemplated.

As used herein with reference to luciferase enzymes, the term "substrate" means the reactive substrate molecule upon which the luciferase acts, excluding any additional cofactors that may be beneficial to, or required for, binding of the luciferase to the substrate and/or catalysis. For example, luciferase catalysed reactions may require or benefit from cofactors such as magnesium, CoA and ATP, however in the context of the present invention such cofactors are not considered to fall within the scope of the term "substrate". Luciferase "substrates" include for example D-luciferin and coelenterazine. For the purposes of the present application the term "luciferin" refers to the substrate D-luciferin and its analogues, which molecules are substrates for luciferases derived from, for example, *Coleoptera*, such as firefly, click beetles and railroad worms. In the context of the present invention the term luciferin does not encompass coelenterazine, which represents a different luciferase substrate utilized by a distinct class of luciferase (such as those derived from *Renilla, Gaussia* and *Metridia* for example).

As used herein the term "sample" means any sample, including but not limited to cells, organisms, lysed cells, extracts or components of cells or organisms, extracellular fluid, and media in which cells are cultured, wherein the sample contains or is suspected to contain a luciferase(s) enzyme.

As disclosed herein, the inventors have described for the first time the effect of reducing agents on the activity of luciferase enzymes that are, in their native form, secreted. Indeed, contrary to the effect observed on intracellular luciferases such as *Renilla*- and *Coleoptera*-derived luciferases (wherein the glow reaction is extended in the presence of DTT), the inventors have surprisingly determined that reducing agents such as DTT have the opposite effect on luciferases that are secreted in their native form. That is, reducing agents markedly shorten the period of luminescence generated from luciferases that are secreted in their native state. Additionally, the inventors have surprisingly determined that inactivation of naturally secreted luciferases by reducing agents does not occur immediately, but rather is time-dependent.

Without wishing to be limited by theory, it is postulated herein that whereas intracellular luciferases are well adapted to a reducing environment and benefit from reducing agents in terms of the duration of luminescence, naturally secreted luciferases are adapted to a more oxidising environment and are inactivated by reducing agents, which alter the protein conformation and/or break critical disulfide bonds thereby reducing or abolishing catalytic activity. Importantly, this conversion does not begin immediately after combining the reagents with the luciferase, such that flash measurements are not impeded. The change in conformation may comprise a change in protein folding and/or a change in redox state of the luciferase. Further, the conformational change may comprise the destruction of one or more disulphide bridges in the luciferase protein. A change in state or conformation of a luciferase enzyme may be desired or required in a number of circumstances. Such circumstances include, for example, the use of multi-luciferase assays, the removal of unwanted signal that persists after measurement so that the sample can be applied to other (non-luciferase) assays that utilize luminescence or fluorescence as a read-out, or simply the reduction in light leakage that occurs from a previously measured well into a currently measured well.

Embodiments of the invention find application in any luciferase-based reaction where it is desirable to determine or quantify the amount and/or activity of the luciferase enzyme. For example, embodiments of the invention are particularly, but not exclusively, applicable for use in reporter gene assay systems utilising destabilizing elements so as to provide a rapid response in addition to high signal strength. Whilst in embodiments of the invention a sample to be analysed may be known to express a given luciferase, such as a luciferase that is, in its native form, a secreted luciferase, this need not be the case. For example, those skilled in the art will appreciate that a given sample may not be known to contain a luciferase enzyme in question. For example a cell may be known to possess (and may have been transformed with) an expression construct comprising a polynucleotide encoding the luciferase, optionally operatively linked to a promoter, enhancer or other regulatory sequence, but it may not be known that the luciferase enzyme is expressed. Therefore included within the scope of the present invention are embodiments where the sample to be analysed is suspected to express a particular luciferase.

In addition to reporter expression assays as described herein, embodiments of the invention also find application in other assay systems wherein the amount and/or activity of one or more luciferase enzymes are to be determined. For example, the luciferase may be used as a reporter in an immunoassay or as a label in a hybridisation assay and thus may be linked to, for example, an antibody or nucleic acid probe. Thus the luciferase may be used as a reporter or detectable label.

As disclosed herein, it has been found that in the presence of a reducing agent, very high bioluminescent signal strength generated from a naturally secreted luciferase in the first few seconds following addition of substrate can be coupled with a very rapid decline in bioluminescent signal. The reducing agent may be added alone or may be a constituent of a reagent composition such as an assay buffer (for example together with a luciferase substrate(s)) or a cell lysis buffer as described below.

Accordingly, reagent compositions for use in accordance with embodiments of the invention may comprise at least one reducing agent, typically a thiol-based reducing agent.

In a general sense, oxidation-reduction (redox) reactions are characterized by a change in oxidation number, usually by a transfer of electrons. The term "oxidation" typically refers to an increase in oxidation state or number (a loss of electrons). Whereas the term "reduction" refers to a decrease in oxidation state or number (a gain of electrons). An "oxidising agent" is sometimes referred to as an electron acceptor, and a "reducing agent" is sometimes referred to as an electron donor. Reduction may be characterised in a number of ways. In addition to "decrease in oxidation number" or "gain of electrons", reduction can also often be considered as a "gain in hydrogen". For example, a double bond gains two hydrogens when it is reduced and a ketone or aldehyde gains a hydrogen when reduced to a primary or secondary alcohol respectively, and a disulphide bond gains two hydrogens when reduced to two thiols. Substances that have the ability to oxidize other substances are said to be "oxidative" and are referred to as "oxidising agents", "oxidants" or "oxidisers". Substances that have the ability to reduce other substances are said to be "reductive" and are referred to as "reducing agents", "reductants", or "reducers". Typically in a redox process, the reductant or reducing agent loses electrons and is oxidised and the oxidant or oxidising agent gains electrons and is reduced. One or more reducing agents may be present in a reagent composition or in a corresponding reaction mixture in which that reagent is used, in order to provide an overall "reducing" or "reductive" environment in that reagent or reaction mixture.

The reducing agent may promote reduction of the luciferase thereby promoting or otherwise facilitating the conversion of the luciferase from a more active conformation or form to a less active conformation or form.

Those skilled in the art will appreciate that a variety of reducing agents are suitable for the purposes of the present invention and are contemplated herein. For example, the reducing agent may be a disulphide bond converting agent that contributes to the generation of an electrochemical potential in the reagent composition such that disulphide bonds are reduced to thiols, thus denaturing the luciferase protein. By way of example, the reducing agent may be an agent capable of reducing, directly or indirectly, disulphide bonds in the luciferase protein. For example, thiols, as reducing components of redox buffers, are known to affect the rates of thiol-disulphide interchange reactions involved in protein folding and denaturation.

A general equation describing the reduction of thiols is shown in equation 1.0:

$$R-S-S-R^1 + 2H^+ + 2e^- \rightarrow R-SH + R^1-SH \qquad 1.0$$

Examples of suitable reducing agents include but are not limited to: dithiothreitol (DTT); dithioerythritol (DTE); tris (e-carboxyethyl)phosphine (TCEP); thioglycolate; sodium thioglycolate; pyruvate; cysteine; sodium sulphide; hydrogen sulphide; dithionate; hydrogen+platinum catalyst; β-mercaptoethanol; β-mercaptoethylamine; mercaptoacetic acid; thiourea dioxide; N-ethylmaleimide; and ascorbate. In some embodiments the reducing reagent may be immobilised on a solid support, for example a polymer support. An example of an immobilised reducing reagent is immobilised TCEP disulphide reducing gel. TCEP is an example of a reducing agent, which is not a thiol derivative [Willis, M., S., Protein Science, 2005, 14, 1818-1826].

Typically the reducing agent is present at a concentration of at least about 500 μM, 1 mM, 2 mM, 5 mM, 10 mM, 20 mM, 50 mM, 75 mM, 100 mM, 150 mM, 200 mM, 250 mM, 300 mM, 400 mM or 500 mM.

Reagent compositions for use in accordance with the invention may also include numerous additional components as will be readily appreciated and ascertained by those skilled in the art. The identity of such additional components will depend largely on the luciferase enzyme used in the assay and the circumstances and purpose of the assay. One such typical additional component for a reagent composition of the invention is the substrate for the luciferase. By way of example only, reagent compositions may further comprise components suitable for or beneficial in the reaction catalysed by the luciferase and/or the lysis of cells expressing the luciferase. For example, the composition may comprise one or more divalent metal chelators (such as EDTA, CDTA or EGTA), antioxidants (such as ascorbic acid), protease inhibitors (such as oxalic acid), salts, detergents (typically non-ionic), or additional routinely employed buffer components such as HEPES, Tris, BSA and/or glycerol. Additionally, a reagent composition of the invention may have a pH of at least about 7, typically between about 7 and about 9. Determining the exact constitution of a reagent composition to be employed in any particular circumstance, in terms of the additional component(s) to be added, is within the capabilities of the person skilled in the art.

As exemplified herein, various modified luciferase assay buffer compositions, for example including a reducing agent, provide very high initial signal strength when used with a modified intracellular *Gaussia* luciferase or standard secreted *Gaussia* luciferase, followed by a very rapid decline in luminescence to background levels. That the inclusion of a reducing agent shortens the period of luminescence from a secreted luciferase is particularly surprising given that it is contrary, indeed opposite, to the reported effect of DTT on intracellular luciferases such as firefly and *Renilla* luciferases.

Disclosed herein are methods for utilizing this unexpected effect of reducing agents on secreted luciferases, and indeed the differential effect of these agents on different luciferases to advantage. In particular, the inventors' findings have led to the development of novel methods for performing multi-luciferase assays. In accordance with the prior art, the signal generated by different luciferases have been distinguished via the use of quenching reagents or based on differences in emission wavelength. The present invention describes for the first time that luciferase signals can also be distinguished on a temporal basis; i.e. based on differences in their kinetics of light emission. Without wishing to be bound by theory, the data exemplified herein suggest that unlike cytoplasmic luciferases, secreted luciferases require folding in order to adopt their active conformation. Whereas exposure to reducing agents such as DTT reduces or abolishes the activity of the secreted luciferases this process of inactivation takes more than a few seconds and this creates a window of opportunity for measuring the activity of the luciferase before it begins to deactivate. Surprisingly, as exemplified herein the inclusion of up to 50 mM DTT does not cause any reduction in initial signal intensity despite its ability to substantially or completely inactivate the luciferase within about 5 to 15 minutes.

Additional benefits offered by reagent compositions of the present invention include a reduction in background luminescence (in effect a higher signal:noise ratio) and a prolonged shelf-life of the assay reagent. (Assay buffers of the prior art have a limited shelf life after the addition of substrate, presumably due to auto-oxidation.)

Thus, methods of the present invention provide higher sensitivity of detection coupled with short signal duration. This is demonstrated to be the case in luciferases that are secreted in their wild-type state, regardless of whether they are utilised in that wild-type secreted format or are modified to become non-secreted. That the same agents (reducing agents) provide a longer signal duration from intracellular luciferases such as *Renilla* luciferase, presents an opportunity to use these agents to better distinguish luciferase signals based on differences in their kinetics of light emission.

A reagent composition for use in accordance with the invention may further comprise one or more chelators. Suitable chelators include but are not limited to divalent metal chelators such as, for example, EDTA, CDTA and EGTA. The chelator may be present at a concentration of between about 1 mM and about 15 mM.

Those skilled in the art will appreciate that where exemplary ranges or constituents are provided herein, these are not exhaustive but are merely illustrative of ranges and constituents that may be included in compositions of the invention in achieving unfolding of the luciferase protein, enhanced bioluminescent signal intensity, reduced background signal, prolonged reagent shelf-life and/or shortening of bioluminescent signal.

Using methods of the invention, the bioluminescent signal generated by the luciferase can be limited to a short phase that begins within about one second following addition of the luciferase substrate. For example, the bioluminescent signal can be limited to less than about 30 minutes or less than about 15 minutes after addition of the substrate. Further, by way of example only, the bioluminescent signal generated by the luciferase may be such that from 5 minutes, 10 minutes, 15 minutes, 20 minutes, 25 minutes or 30 minutes after initiation of the luciferase-catalysed reaction, the bioluminescent signal is between less than about 1% of the initial signal and less than 0.1% of the initial signal.

The luciferase substrate and the reducing agent may be a constituent of the same reagent composition or may be separate (including constituents of separate reagent compositions) such that they can be added independently. Where the luciferase substrate and the reducing agent are not constituents of the same reagent composition, the substrate may be added to the sample containing luciferase either before, after or at the same time as addition of the reducing agent. In one embodiment the substrate is coelenterazine or a derivative thereof. By way of example, the coelenterazine or derivative thereof may be present in a concentration of more than about 5 µM, more than about 10 µM, more than about 15 µM, more than about 20 µM or more than about 25 µM. Suitable coelenterazine derivatives are well known to those skilled in the art and include, but are not limited to m-, v-, e- and f-coelenterazine.

Typically luciferase-based reporter assay systems employ two buffers, a lysis buffer and an assay buffer (collectively referred to herein as "assay reagents"). The lysis buffer typically comprises components for lysing the cells containing the luciferase to be assayed while the assay buffer typically contains, inter alia, the substrate and any required cofactors for the luciferase reaction.

Reducing agents for use in accordance with methods of the present invention may be constituents of luciferase assay buffers. Advantageously, assay buffers in accordance with the present invention effectively provide a shorter period of light emission when used in conjunction with luciferases that are secreted in their wild-type or native state. Alternatively, reducing agents for use in accordance with methods of the present invention may be constituents of cell lysis buffers. By way of example, it may be advantageous to incorporate a reducing agent into a cell lysis buffer where a method involves measuring two or more luciferases expressed by a cell, wherein one luciferase is secreted and the other is intracellular. Secreted luciferase activity may be measured normally in a sample of the conditioned medium, the cells subsequently lysed in a reagent comprising a reducing agent, and then activity of the intracellular luciferase measured. The present inventors have found that a large portion of secreted luciferase may be intracellular at any given time-point (possibly in the endoplasmic reticulum prior to migration to the cell membrane for secretion). This prevents measurement of the truly intracellular luciferase because the cell lysate contains a mixture of secreted and non-secreted luciferase. By using a lysis buffer with a reducing agent the secreted luciferase located intracellularly is inactivated such that all light emission subsequently measured is known to derive only from the truly intracellular luciferase.

Alternatively, reducing agents may be constituents of a combined lysis and assay buffer such that only a single buffer composition is required to lyse cells, potentially directly within the medium in which the cells are cultured, and initiate the luciferase-catalysed reaction. It will also be appreciated by those skilled in the art that where a secreted luciferase is employed it may be unnecessary to lyse the cells expressing the luciferase. Rather the assay buffer, comprising a reducing agent, may be added directly to the medium in which the cells are cultured so as to initiate the luciferase-catalysed reaction.

Reagent compositions for use in accordance with the present invention may typically be aqueous solutions, or alternatively may be in solid or dry form such as lyophilised. Whether aqueous or lyophilised, reagent compositions of the invention may be provided either comprising all constituents pre-mixed or as a combination of constituents to be mixed prior to use. The reagent composition may be used directly in an assay system for the determination of luciferase amount and/or activity, or may be reconstituted, dissolved, diluted or otherwise treated either chemically or physically such that the composition is capable of performing the desired function.

Methods of the invention and reagent compositions for use in accordance with the present invention are applicable to determining the amount and/or activity of any luciferase in a sample. The luciferase may be a naturally occurring enzyme or a modified or recombinant enzyme. A naturally occurring luciferase may be derived from any one of a number of bioluminescent organisms, typically from the light organ thereof. Such organisms include but are not limited to bioluminescent bacteria, protozoa, coelenterates, molluscs, fish, flies, crustaceans and beetles. Conventionally, luciferases may be categorised according to the substrate utilised by the enzyme. One group of luciferases such as those of fireflies and click beetles utilise luciferin. A second group of luciferases, such as those of the marine organisms *Renilla, Gaussia* and *Pleuromamma* utilise coelenterazine. *Vargula* luciferase utilises a different substrate. The reagent compositions of the present invention are applicable to use with luciferases using either luciferin or coelenterazine as a substrate.

The methods and reagent compositions are similarly applicable to use with either intracellular or secreted luciferases. Firefly and *Renilla* luciferases are intracellular in their natural state, whereas *Gaussia* luciferase is secreted in its wild-type state. *Gaussia* luciferase is of particular interest as it has been shown to yield a bioluminescent signal strength higher than that achievable with *Renilla* luciferase and is the smallest known luciferase. Other secreted luciferases have also been shown to yield strong signal strength, for example *Metridia longa* luciferase. Typically, the reagent compositions of the invention are used in conjunction with at least one secreted luciferase. In some embodiments, the reagent compositions of the invention are used in conjunction with at least one secreted luciferase and at least one non-secreted luciferase Suitable luciferases are readily obtainable by those skilled in the art using known techniques. The luciferase may be directly obtained from the light organ(s) of the bioluminescent organism. Alternatively the luciferase may be obtained from cultured cells, for example bacteria, yeast, insect cells or mammalian cells which have been transformed with nucleic acids encoding the luciferase.

The luciferase may be a recombinant enzyme such as a variant or derivative of a naturally occurring luciferase. By way of example, a naturally secreted luciferase may be modified using standard molecular biological techniques by removal of signal sequences and/or fusion to an intracellular polypeptide such that the enzyme is no longer secreted but remains intracellular. Alternatively, or in addition, a number of other modifications well known to those in the art may be made, for example, to alter one or more amino acids in the luciferase polypeptide sequence to modulate expression and/or solubility of the enzyme in a cell culture system of choice. Such modulation may be an increase or decrease in expression and/or solubility, depending on the requirements of the particular application in which the luciferase, and the reagent compositions of the invention are to be employed. For example, it may be desirable to modify the luciferase by the introduction of one or more destabilising elements to destabilise the protein. Luciferases containing destabilising elements have shortened half-lives and are expressed at lower steady-state levels than luciferases which do not contain such elements. Suitable protein destabilising elements include PEST sequences (amino acid sequences enriched with the amino acids proline (P), glutamic acid (E), serine (S) and threonine (T)), a sequence encoding an intracellular protein degradation signal or degron, and ubiquitin. The enhanced sensitivity attained with embodiments of the present invention are particularly advantageous for use with destabilized luciferases given the lower steady state expression levels of such luciferases. Any suitable method for destabilising a protein is contemplated herein. Suitable methods are described, for example, in co-pending U.S. patent application Ser. No. 10/658,093 (the disclosure of which is incorporated herein by reference in its entirety). Expression of the luciferase may also be modified by, for example, the addition of sequences such as poly(A) tails, transcriptional or translational enhancers, and/or adapting codon usage in the encoding polynucleotide sequence for a particular expression system. For example, to optimise expression of the luciferase in insect cells or human cells, codon usage in the luciferase polynucleotide may be optimised for insect or human cells respectively. Approaches for codon usage adaptation and optimisation for different species are well known to those skilled in the art.

Further modifications that may be made to luciferase polypeptide or polynucleotide sequences are also well known to those skilled in the art. For example, restriction enzyme cleavage sites may be introduced into the polynucleotide, or the luciferase polypeptide may be fused or conjugated with a second polypeptide of different function such as a selectable marker (e.g. antibiotic resistance).

Those skilled in the art could readily predict using well known techniques such as computer modelling, those luciferases which are particularly amenable to use in accordance with the invention, as well as predict the modifications that may be made to a secreted luciferase the render the luciferase non-secreted. For example, luciferases that are secreted in their native form typically comprise cysteine residues that form disulphide bridges in the mature active conformation of the protein. The cysteine residues may be arranged in spacing patterns that are repeated within the amino acid sequence such that they can be predicted to form intramolecular disulphide bonds. Such luciferases typically show reduced activity when expressed intracellularly. Thus, those skilled in the art will appreciate that homologous luciferases sharing one or more of these characteristics of naturally secreted luciferases are particularly suitable for use in accordance with the present invention.

When using secreted luciferases in in vitro reporter assays, a sample of the cell culture medium, rather than a cell lysate, is typically taken for measurement of luciferase activity. Whilst advantageous in some applications (e.g. repeated measurements from the same cells), secreted luciferases are not appropriate for other applications. In particular, the secreted luciferase can accumulate in the cell culture medium such that rapid changes in gene expression can not be monitored accurately. Mutant, non-secreted forms of these luciferases (preferably containing destabilizing elements) overcome this limitation. One particular modified luciferase described herein is a modified *Gaussia* luciferase in which the 14 amino acid N-terminal signal peptide is deleted thereby generating a non-secreted luciferase. A second modified luciferase described herein is a modified *Metridia* luciferase in which the 17 amino acid N-terminal signal peptide is deleted thereby generating a non-secreted luciferase. Other secreted luciferases can be similarly modified for intracellular expression, particularly in eukaryotes, using a variety of methods well known to those skilled in the art.

In accordance with the present invention, luciferase activity can be detected and measured by any one of a number of methods well known to those skilled in the art, including but not limited to using a luminometer, a scintillation counter, a photometer such as a photomultiplier photometer or photoemulsion film.

Dual- and Multi-Luciferase Reporter Assays

In providing, inter alia, for the generation of higher sensitivity (stronger flash phase and lower background signal) and a faster rate of luminescent signal decay in the case of secreted luciferases than is achievable using currently available systems, methods and compositions of the present invention find particular application in dual- and multi-luciferase reporter assays. Secreted luciferases, such as *Gaussia* luciferase provide a higher bioluminescence signal strength than normally non-secreted, intracellular luciferases. However, a dual- or multi-luciferase assay utilizing *Gaussia* luciferase, or indeed any other secreted luciferase, has not previously been described.

In many applications, such as high throughput drug screening, which can involve screening libraries of millions of compounds, dual-luciferase assays can provide considerable savings in cost and time, compared to performing two experiments separately. On the other hand, single reporter assays are invariably less expensive and/or simpler to perform than dual-luciferase assays such that users may choose to perform a single luciferase assay, even when the cell line used expresses multiple luciferases. Indeed in reiterative processes such as high throughput drug screening, for example, it may be desirable to perform a single luciferase assay initially in large initial screen of the test promoter, in order to select a short-list of candidate compounds. This may be then followed by a dual luciferase assay including a control reporter, performed on a smaller number of samples. Thus, it is preferable to have a dual-luciferase assay system that allows the user to choose between measuring test reporter only or both test reporter and control reporter.

In an embodiment of the invention, at least one of the luciferases (the first luciferase) in a dual- or multi-luciferase assay in accordance with the invention is a luciferase that in its "wild-type state" (hereinafter "native form") is not cytoplasmic. Native form in this context means in the unmodified organism from which the luciferase is derived. In other words, the term "native form" makes reference to the normal site or location at which the mature wild-type luciferase undergos its catalytic reaction in nature. A suitable luciferase of this type would typically operate (undergo the light-emitting reaction) in an environment or microenvironment that is not reducing; or is at least less reducing (more oxidising) than the cytoplasm. The cellular compartment within the endoplasmic reticulum is one such microenvironment. Another is the plasma membrane, insofar as the catalytic domain(s) of the luciferase may be situated on the extracellular side of the plasma membrane.

Typically, though, the luciferase in its active native form is extracellular; more typically it is secreted. It may be secreted into an extracellular or other environment within the organism, provided that environment into which it is secreted or in which it normally undergoes its catalytic activity is not a reducing environment in comparison to the cytoplasm of eukaryotic cells, such as mammalian cells. More typically, the luciferase in its native form is secreted into the external environment. Even more typically, the luciferase is derived from an aquatic organism that secretes luciferase into its water environment. Most typically, the luciferase is derived from a marine organism that secretes luciferase into the sea-water. Such luciferases typically utilize coelenterazine as a substrate. The abovementioned characteristics of the first luciferase apply to that luciferase when in its native form. Suitably, the luciferase may be modified to remove one or more of such characteristics. Such luciferases are well known in the art as described herein.

The second luciferase is typically a luciferase that in its native form would normally operate (undergo the light-emitting reaction) in an environment or microenvironment that is reducing; or is at least more reducing (less oxidising) than that of the first luciferase. Typically, the luciferase in its native form is cytoplasmic. Suitable luciferases are well known to those skilled in the art. It may be derived from an aquatic organism or a terrestrial organism. It may use the same substrate as the first luciferase or a different substrate. It may emit light of the same wavelength as the first luciferase or of a different wavelength.

In accordance with an embodiment of the invention, exemplary features that may distinguish the first luciferase from the second luciferase as defined above are as follows:

(a) The redox potential of the natural microenvironment in which the first luciferase normally undergoes its catalytic activity is typically more reductive and less oxidative than that natural microenvironment in which the second luciferase undergoes its catalytic activity, and/or;

(b) The natural microenvironment in which the first luciferase normally undergoes its catalytic activity is typically extracellular, whereas the natural microenvironment in which the second luciferase undergoes its catalytic activity is intracellular, and/or;

(c) In their native forms the first luciferase is secreted, whereas the second luciferase is not secreted, and/or;

(d) The effect of a reducing agent or a reducing redox environment on the first luciferase is inactivation, at least to a greater degree than with respect to the second luciferase, and/or;

(e) The activity of the first luciferase is dependent on the formation of intramolecular disulphide bridges whereas the activity of the second luciferase is not, and/or;

(f) The first luciferase contains cysteine residues that are critical for formation of its secondary/tertiary structure, and/or;

(g) The predicted structure of the properly folded first luciferase comprises multiple disulphide bridges between cysteine residues whereas the predicted structure of the second luciferase does not, or at least not in the region of the catalytic domain.

In some embodiments, additional luciferases are also utililized such that three, four, five or more different luciferases are measured in a single sample. Typically in these embodiments, at least the third and subsequent luciferases are of the type described for the second luciferase; i.e. tolerant of a reducing environment. The multiple luciferases may emit light at different wavelengths and/or may be derived from different organisms. By way of example only, in a triple luciferase assay the second luciferase may be derived from *Coleoptera* and the third luciferase may be derived from *Diptera*.

Examples of multi-luciferase assays contemplated by the present invention are described below.

(i) Double-Luciferase Assay Using Two Different Substrates and One or Two Different Assay Buffers In one embodiment, the first luciferase is a secreted marine luciferase (e.g. *Gaussia* luciferase) that utilizes coelenterazine as a substrate and the second luciferase is a terrestrial luciferase (e.g. firefly, click beetle or *Diptera* luciferase) that utilizes luciferin as a substrate. To a sample containing both luciferis is first added a coelenterazine-containing assay buffer with a reducing agent as described and exemplified in accordance with the present invention. Light emission is measured immediately and then the sample left standing or stored for about 5 minutes or more to allow the *Gaussia* signal to decay, preferably to near zero. A luciferin-containing assay buffer (that may also include Mg, CoA and ATP) is then added and light emission measured again. The first reading is a measure of *Gaussia* luciferase activity and the second reading is a measure of firefly or click beetle activity.

In accordance with the above, the present invention provides a method for determining the amount or activity of a first and second luciferase in a sample, the method comprising (a) contacting the sample with reactive substrates for the first and second luciferases and a reducing agent that time dependently inactivates the first luciferase but does not inactivate the second luciferase;

(b) measuring the luminescent signal before the first luciferase is inactivated by the reducing agent;

(c) measuring the luminescent signal after the first luciferase is inactivated; and (d) using the data collected in (b) and (c) to calculate the amounts or activities of each luciferase relative to each other or relative to other samples.

Also contemplated is a method for determining the amount or activity of a first and second luciferase in a sample, the method comprising (a) contacting the sample with a reactive substrate for the first luciferase and a reducing agent that time dependently inactivates the first luciferase but does not inactivate the second luciferase;

(b) measuring the luminescent signal before the first luciferase is inactivated;

(c) contacting the sample with a reactive substrate for the second luciferase;

(d) measuring the luminescent signal after the first luciferase is inactivated; and (e) using the data collected in (b) and (c) to calculate the amounts or activities of each luciferase relative to each other or relative to other samples.

luciferase relative to each other or relative to other samples.

(ii) Triple-Luciferase Assay Using Two Different Substrates and Two Different Assay Buffers In one embodiment, the first luciferase is a secreted marine luciferase (e.g. *Gaussia* luciferase) that utilizes coelenterazine as a substrate and emits blue light and the second and third luciferases are terrestrial luciferases that utilize luciferin as a substrate and emit green and red light, respectively; for example, red and green Phrixothrix luciferases and/or those available from TOYO B-net (Japan). To a sample containing both luciferases is first added a coelenterazine-containing assay buffer with a reducing agent as described and exemplified in accordance with the present invention. Light emission is measured immediately (no filters required) and then the sample left standing or stored for about 5 minutes or more to allow the *Gaussia* signal to decay, preferably to near zero. A luciferin-containing assay buffer (that may also include Mg, CoA and ATP) is then added and light emission measured again using filters to distinguish the red and green signals. Simultaneous measurement of red and green light is possible with some luminometers, whereas others require sequential measurement.

(iii) Quadruple-Luciferase Assay Using Two Different Substrates and Two Different Assay Buffers In an embodiment of the invention the multi-luciferase assay as described in (ii) above may further include as a fourth luciferase, one that utilizes luciferin as a substrate but which emits orange light; e.g. the Rol luciferase available from TOYO B-net. During the second measurement appropriate filters are used to separate the green, orange and red signals; for example as described for the Multicolor-Luc Assay system (TOYO B-net).

(iv) Pentuple-Luciferase Assay Using Two Different Substrates and Two Different Assay Buffers In an embodiment of the invention the multi-luciferase assay as described in (iii) above further including as a fifth luciferase, one that emits blue light but is a cytoplasmic luciferase in its native form. Most such luciferases utilize coelenterazine as a substrate and are of marine origin; for example, *Renilla* luciferase. During the first measurement, both *Gaussia* and *Renilla* emit light, such that this measurement is the combined total of *Gaussia* and *Renilla* signals. Just prior to adding the second assay reagent, an additional measurement is made. At this time the *Gaussia* signal has decayed such that the entire signal is from *Renilla* luciferase. The *Gaussia* and *Renilla* signals are then calculated (for example as described in Example 7 herein). The second assay buffer (that includes luciferin and optionally Mg, CoA and ATP) is then added and light emission measured again using filters to distinguish the green, orange and red signals and separate them from any remaining blue signal. Alternatively, the second assay buffer may contain a quenching agent for *Renilla* luciferase in order to terminate the remaining blue signal.

Alternatively, the *Renilla* only signal can be measured after addition of the second assay buffer using appropriate filters to separate its blue emission from the other colours. In this case, the blue filter may also be used in the first measurement.

(v) Multi-Luciferase Assays Using Two Different Substrates Combined in a Single Assay Buffer In accordance with an embodiment of the invention, assays may be performed as described in (i) to (iv) above, except that the two assay buffers are combined into a single buffer comprising coelenterazine, luciferin, a reducing agent, Mg and optionally ATP and CoA. Four filters are used to separate the blue, green, orange and red signals. The blue signal is measured first (using blue filter to exclude other wavelengths) and preferably a delay of about 5 minutes or more is included before measurement of the other colours in order to minimise any cross-talk from the *Gaussia* signal, which is very strong in the initial stages only.

(vi) Double-Luciferase Assay Using One Secreted and One Non-Secreted Luciferase

In one embodiment, the first luciferase is a secreted marine luciferase (e.g. *Gaussia*) in its secreted form and the second luciferase is an intracellular marine luciferase (e.g. *Renilla*). Cells expressing both luciferases are cultured and a sample of the conditioned medium is removed for measurement of the secreted (*Gaussia*) luciferase. The cells are lysed in a reagent comprising a reducing agent and later measured for the intracellular (*Renilla*) luciferase. With standard reagents, light emitted from the cell lysate would comprise an indistinguishable combination of light derived from both the *Renilla* luciferase and the subset of *Gaussia* luciferase that has been produced but not yet secreted. By including a reducing agent in the lysis buffer, the *Gaussia* luciferase is inactivated such that light emission is a measure of *Renilla* luciferase levels.

Also contemplated by the present invention are further methods for determining the amount or activity of two or more different luciferases in a sample. In one embodiment the method comprises contacting the sample with a reagent composition that comprises reactive substrates for at least two of the luciferases, determining the amount of light emitted at two or more different time points, and using the data collected to calculate the amounts or activities of each luciferase relative to each other or relative to other samples; wherein the calculation relies on differences between the two luciferases with regard to the kinetics of light emission in the presence of a reducing agent that inactivates, in a time-dependent manner, at least one of the luciferases. The method may further comprise using differences in wavelength of light emission of the luminescent signal generated by the luciferases to distinguish the signal of at least two of the different luciferases.

Methods of the invention provide improved kinetics of bioluminescence in luciferase reactions and offer advantages over the prior art by virtue of the unexpected finding that reducing agents inactivate, in a time-dependent manner, luciferases that, in their native form, are secreted. Reducing agents may be used in luciferase assays according to the invention, in preparing assay reagents and test kits according to the invention, and in standards and controls for assays and kits according to the invention. The present invention provides kits for carrying out assays of luciferase activity, such kits containing reducing agents for use in accordance with the invention as described herein. Kits of the invention comprise, in one or more physical containers and typically packaged in a convenient form to facilitate use in luciferase assays, suitable quantities of reagent compositions or constituents thereof for carrying out luciferase assays. Luciferase substrates and reducing agents may be in the same or different containers and in the same or different reagent compositions. Typically, the luciferase substrate is provided in a separate container to the assay reagent (minus substrate) in order to prolong shelf life, but is intended to be mixed with the assay reagent prior to use. Multiple reagent compositions, or various constituents of reagent compositions may be combined, for example in aqueous solution or lyophilised, in a single container or in multiple containers. Kits of the invention typically also comprise controls and standards to ensure the reliability and accuracy of assays carried out in accordance with the invention. Suitable controls and standards will be known to those skilled in the art.

In some embodiments reagent compositions to be used in accordance with the invention are provided as separate components within a kit for improved versatility of use. For example, by providing the reducing agent as a separate component, the user can select between:

(a) adding the reducing agent to the lysis buffer for use in accordance with vi) above. As a further example of utility, users working with stable cell lines that express a non-secreted *Gaussia* luciferase in combination with other luciferases can select between measuring the *Gaussia* luciferase or not measuring the *Gaussia* luciferase. In the latter case, the user can utilise lysis buffer with reducing agent to inactivate the *Gaussia* luciferase prior to measuring the other luciferases;

(b) adding the reducing agent to the assay buffer for use in accordance with i) above;

(c) first adding to the sample the assay buffer without reducing agent, measuring luminescence and then adding the reducing agent to inactivate at least one luciferase; and (d) first adding to the sample the assay buffer without reducing agent, waiting until a glow phase is achieved, adding the reducing agent or assay buffer containing reducing agent, and measuring luminescence before the luciferase is inactivated.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Part I: Reducing Agents Shorten Kinetics of Light Emission from Luciferases that are Secreted in Their Native State

Example 1

HeLa cells stably expressing non-secreted and destabilized *Gaussia* luciferase were plated onto 96-well plates and incubated overnight. The non-secreted luciferase is a modified *Gaussia* luciferase in which the 14 amino acid N-terminal signal peptide has been deleted. The destabilised luciferase is an enzyme containing a destabilising element such that it has a shortened half-life and is expressed at lower steady-state level than in the absence of the destabilising element.

Figure 1B:
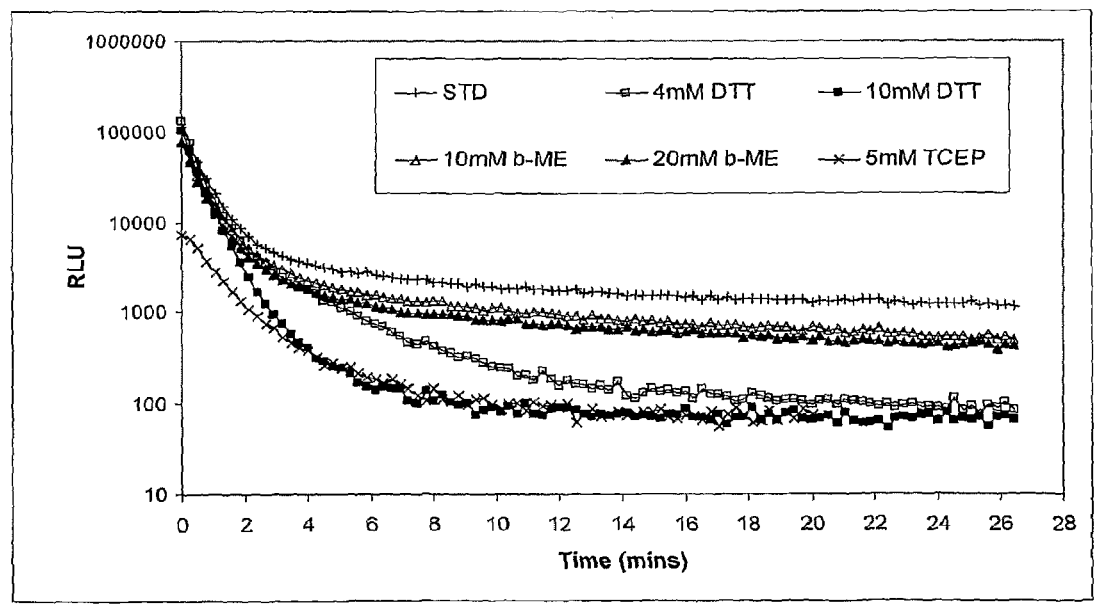

Following the overnight incubation, medium was removed and the cells lysed in 20 ul lysis buffer comprising 25 mM Tris pH 8.1, 150 mM NaBr, 1 mM EDTA, 63.4 uM sodium oxalate, 0.1% NP40 substitute, 5% glycerol (GSv3). Luciferase activity was measured in a kinetic assay following injection of 60 ul of an assay buffer comprising 25 mM Tris pH 8.1; 1 mM EDTA, 2 mM Ascorbate and 26 uM Cz (STD), or the same assay buffer but also containing a reducing agent. Various concentrations of three reducing agents were used: DTT (4 mM, 10 mM, 20 mM or 50 mM); β-mercaptoethanol (10 mM, 20 mM, 50 mM, or 100 mM); and TCEP (500 uM or 5 mM). The results of two independent experiments are shown in FIGS. 1A and 1B. It can be seen that each of the reducing agents caused a more rapid decay in luminescent signal over time (at all concentrations tested) than was observed in the absence of reducing agent. The effect was strongest at higher concentrations of a given reducing agent. The concentration of luciferase substrate used was significantly higher than that normally employed for coelenterazine-utilizing luciferases (approximately 5 µM). The inventors have determined that this higher concentration produced beneficial effects in terms of bioluminescence generated by *Gaussia* luciferase.

Example 2

Figure 2A:
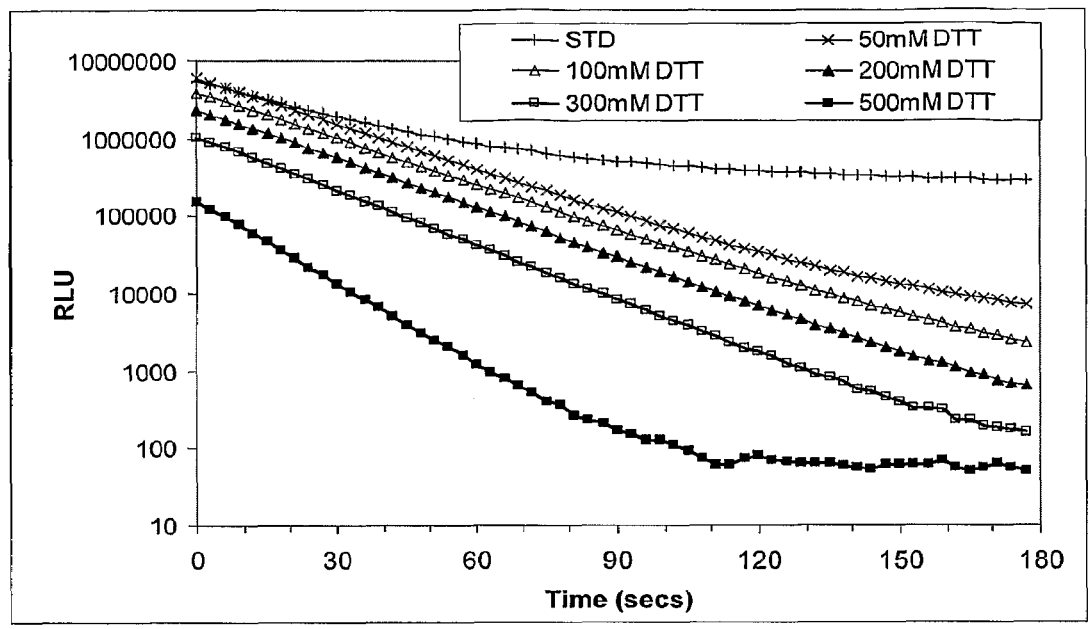
FIGS. 2A-B show the kinetics of bioluminescence in relative light units (RLU) over time for a non-secreted *Gaussia* luciferase in the presence of varying concentrations of DTT. Data is provided over two time courses, up to 180 seconds (A) and up to 33 minutes (B).
Figure 2B:
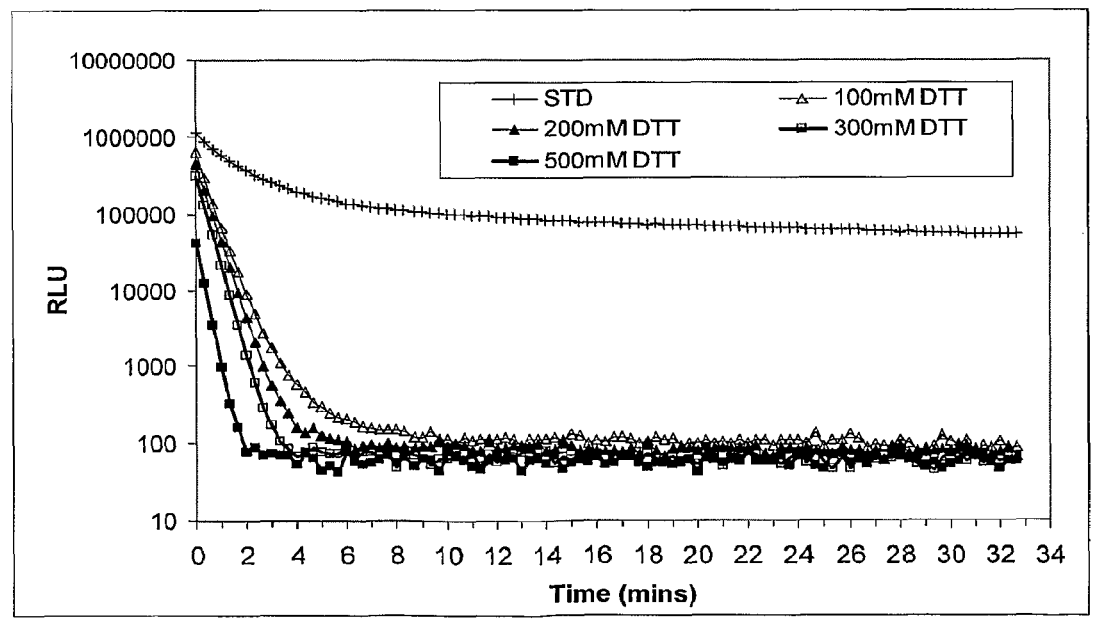

Similar experiments were performed as described in Example 1, however using a broader range of concentrations of DTT in the assay buffer (50 mM to 500 mM). Results from two independent experiments are shown in FIG. 2, representing a short time-course (FIG. 2A) and a longer time-course (FIG. 2B). As observed in the experiments described in Example 1, the rate of decay in luminescent signal was directly related to the concentration of DTT. This effect was seen up to the maximum concentration of 500 mM (FIG. 2A). In the longer time-course (FIG. 2B) the signal dropped to approximately background levels (~100 RLU) within 10 minutes of initiation at all concentrations. This represents a decrease in light intensity of 1,000 to 10,000 times. Importantly, the observation that DTT shortens the period of light emission from *Gaussia* luciferase is contrary to that reported for intracellular luciferases, including firefly and other *Coleoptera* luciferases and *Renilla* luciferases.

Example 3

Figure 3:
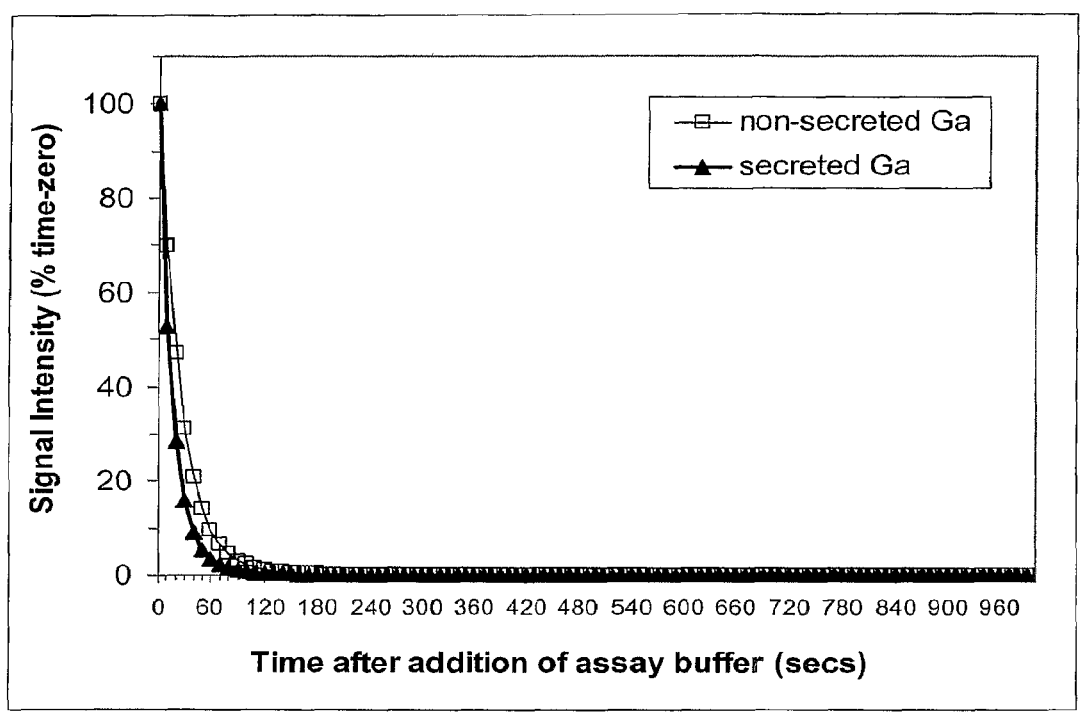
FIG. 3 shows the effect of DTT (50 mM) on the bioluminescent signal from secreted and non-secreted *Gaussia* luciferase.

Similar experiments were performed as described in Example 1 with the exception that the effect of DTT on the time course of luminescence was also investigated for the wild-type secreted *Gaussia* luciferase. This was achieved by transiently transfecting HeLa cells with a reporter plasmid encoding the wild-type *Gaussia* luciferase protein and harvesting the conditioned medium 24 hrs later. The assay buffer (with either 50 mM DTT or no DTT) was injected into wells containing 20 ul of the conditioned medium. Results were expressed as the % signal remaining compared to time zero (see FIG. 3). The data confirm that both forms of the *Gaussia* luciferase (native secreted and modified non-secreted) yield a very rapid decline in light emission when DTT is included in the assay buffer.

Example 4

Figure 4:
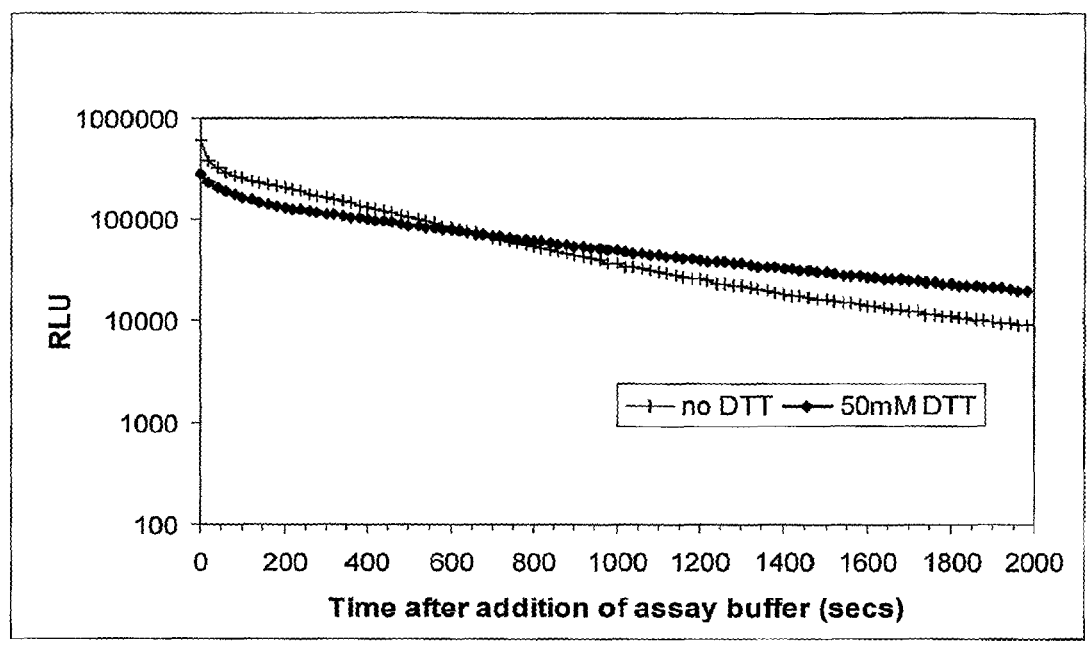
FIG. 4 shows the kinetics of bioluminescence in relative light units (RLU) over time for *Renilla* luciferase in the presence of 50 mM DTT.
Figure 5A:
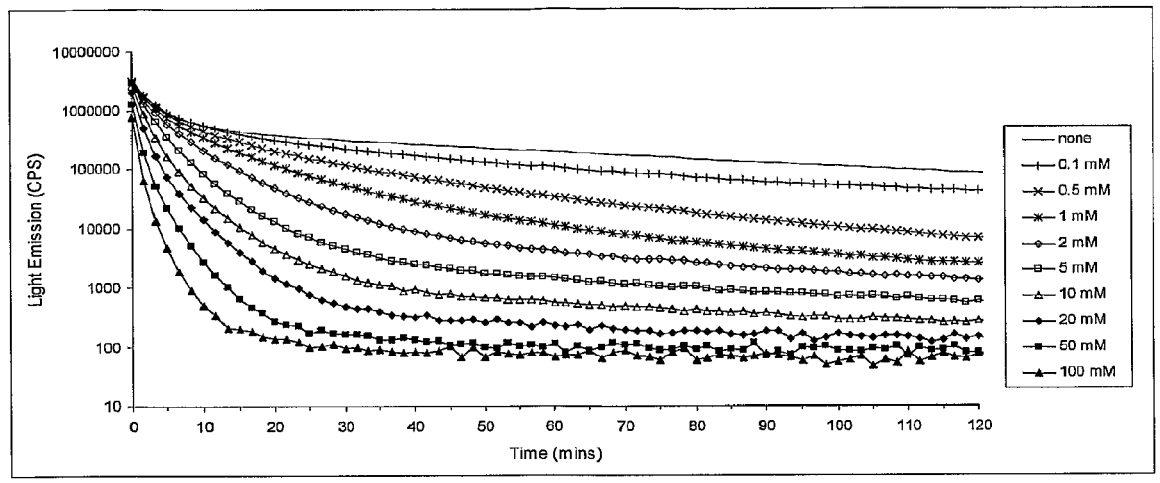
FIGS. 5A-D show the light emission in counts per second (CPS) over time for (A) a non-secreted *Gaussia* luciferase, (B) a secreted *Gaussia* luciferase, (C) a non-secreted *Metridia* luciferase and (D) a secreted *Metridia* luciferase in the presence of varying concentrations of DTT. Data is provided up to 120 minutes.
Figure 5B:
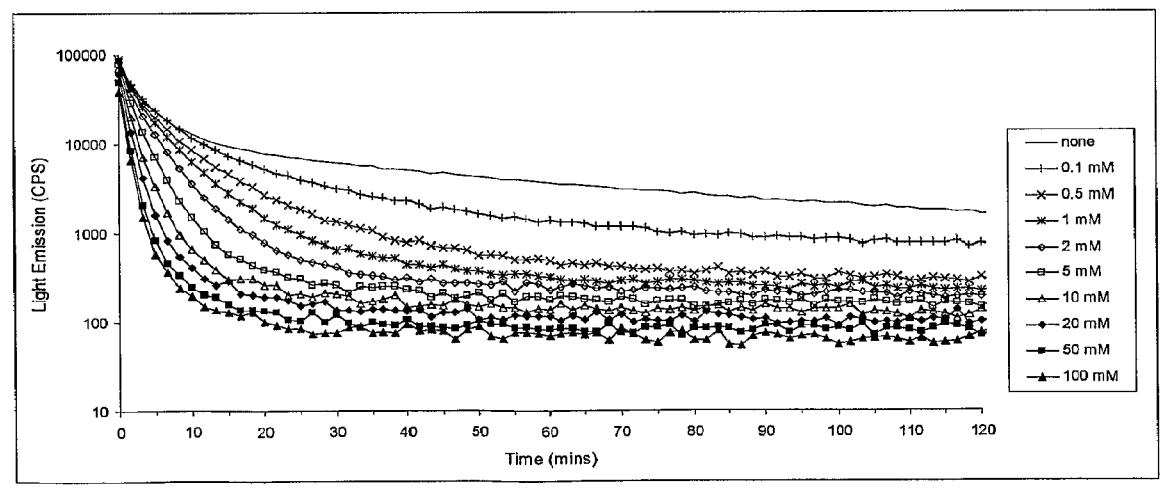
Figure 5C:
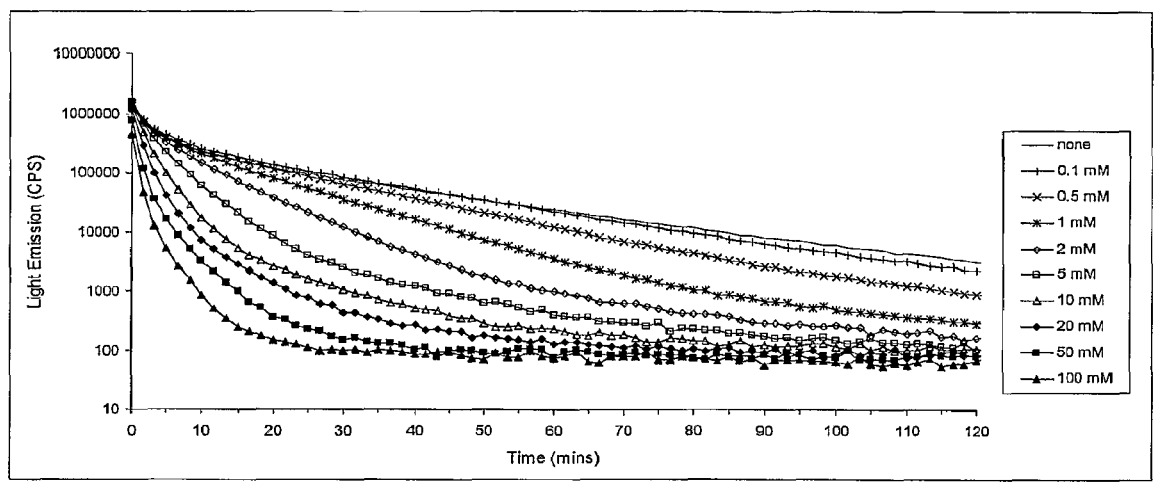
Figure 5D:
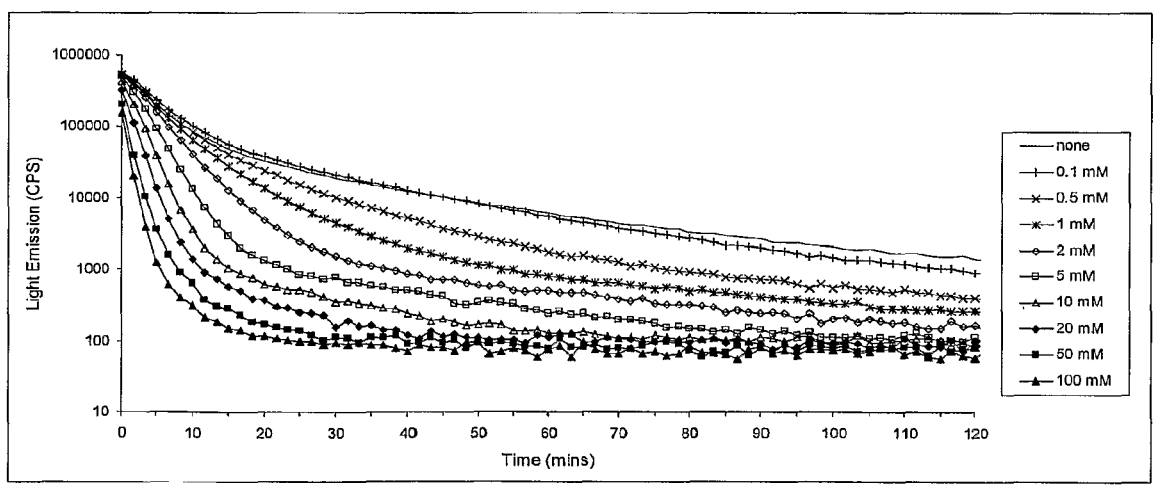

Similar experiment to those described in Example 1 were performed, with the exception that the HeLa cells transiently expressed the intracellular *Renilla* luciferase. A kinetic assay was performed after injection of assay buffer (with 50 mM DTT or no DTT) into wells containing 20 ul of lysate. As shown in FIG. 4, in direct contrast to the effect of DTT on the kinetics of light emission from *Gaussia* luciferase, DTT actually prolongs the light emission from *Renilla* luciferase.

Example 5

HeLa cells were transiently transfected with expression plasmids encoding either *Gaussia* or *Metridia* luciferases in either their native secreted form or a modified non-secreted form. Secreted *Metridia* luciferase was obtained from Clontech and non-secreted *Metridia* luciferase was created in an analogous way to non-secreted *Gaussia* luciferase. The coding region was obtained by PCR using primers that delete the first 16 amino acids after ATG (the secretion signal) and the stop codon. The PCR product was ligated into a pRR23.1 plasmid (GeneStream, AU) to create a non-secreted but destabilized *Metridia* luciferase.

One day after transfection conditioned medium was removed for the secreted luciferases and the non-secreted luciferases were lysed as described in Example 1. Aliquots (20 ul) of conditioned medium or lysate were assayed for luciferase activity in kinetic assays following manual injection of assay buffer comprising the indicated concentrations of DTT in 25 mM Tris pH 7.75; 1 mM EDTA; 2 mM Ascorbic acid and 26 uM coelenterazine.

FIGS. 5A to 5D show that non-secreted and secreted *Metridia* luciferases and non-secreted and secreted *Gaussia* luciferases respond in the same way with a very rapid decline in light emission when DTT is included in the assay buffer. In addition, as shown in FIGS. 5A to 5D there is a concentration-dependent effect of DTT in shortening the period of light emission from all four luciferases.

Example 6

Figure 6A:
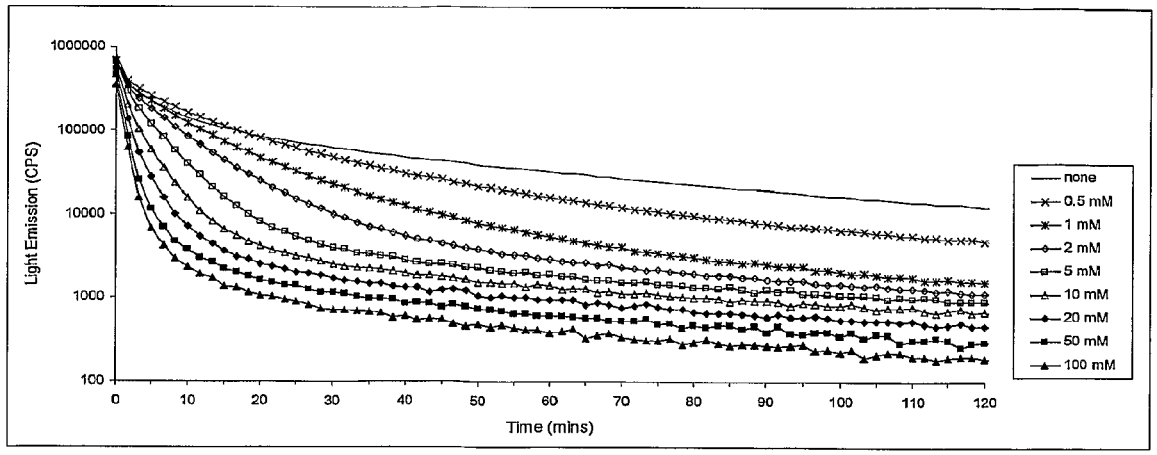
FIGS. 6A-G show the light emission in counts per second (CPS) over time for (A to C) non-secreted *Metridia* luciferase and (D to G) non-secreted *Gaussia* luciferase in the presence of varying concentrations of reducing agents: (A and D) with dithioerythritol (DTE); (B) with sodium sulfite; (C and E) with cysteamine; (F) with TCEP; and (G) with β-mercaptoethanol. Data is provided up to 120 minutes (A to C) and up to 50 minutes (D to G).
Figure 6B:
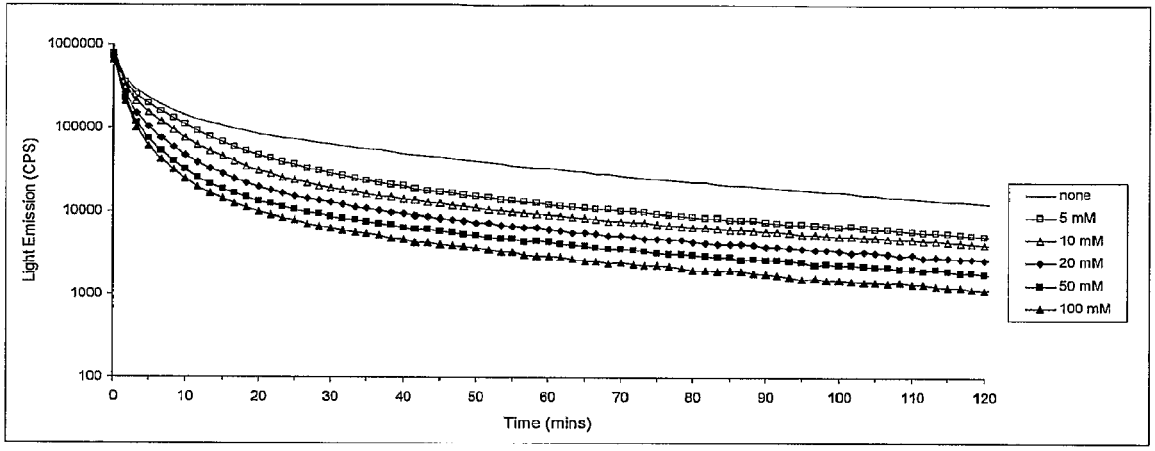
Figure 6C:
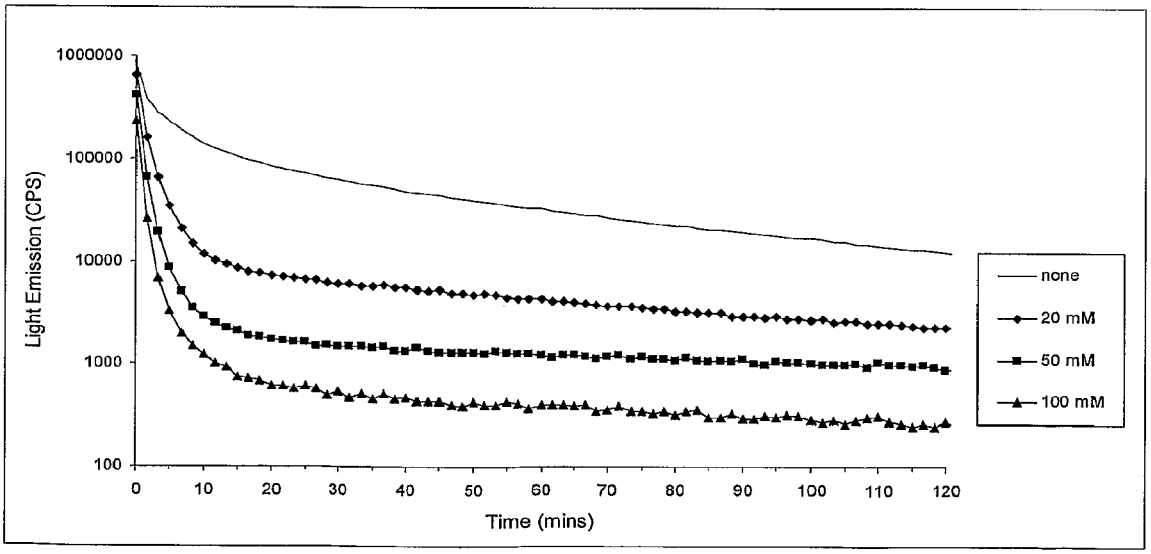
Figure 6D:
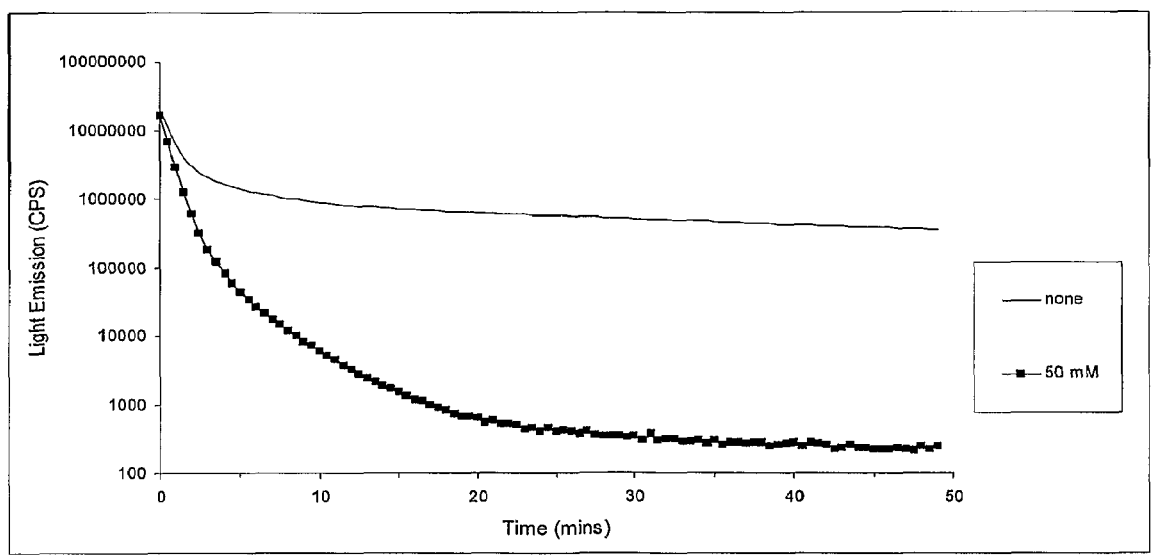
Figure 6E:
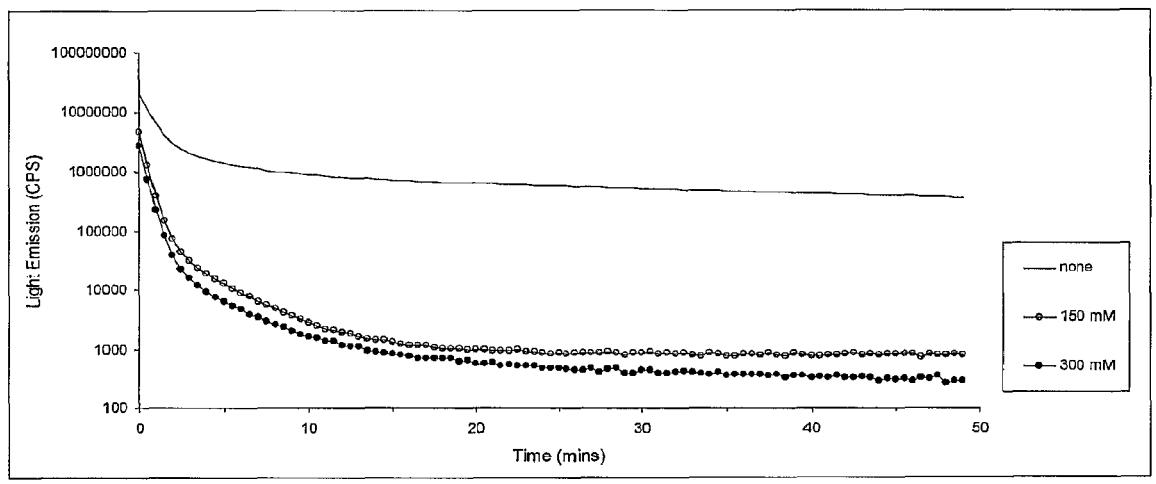
Figure 6F:
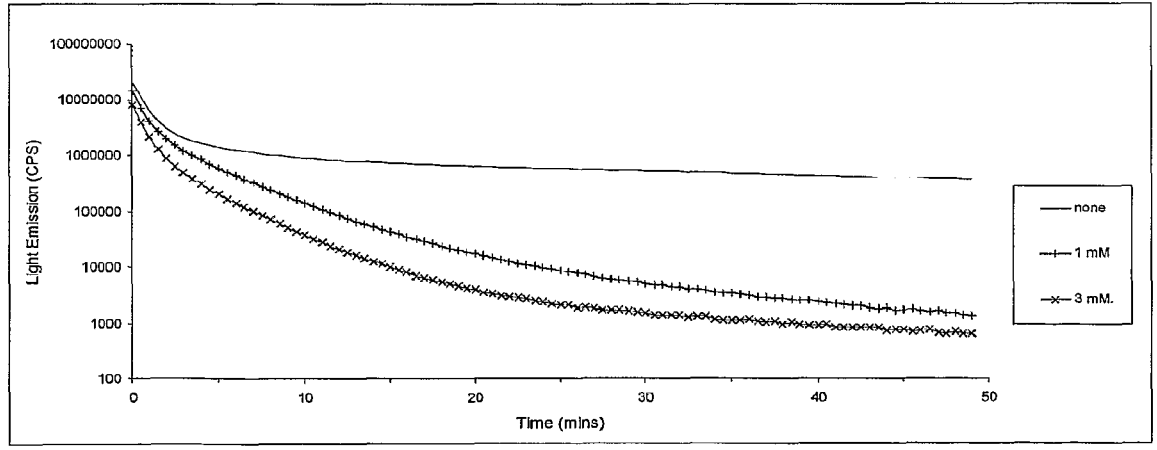
Figure 6G:
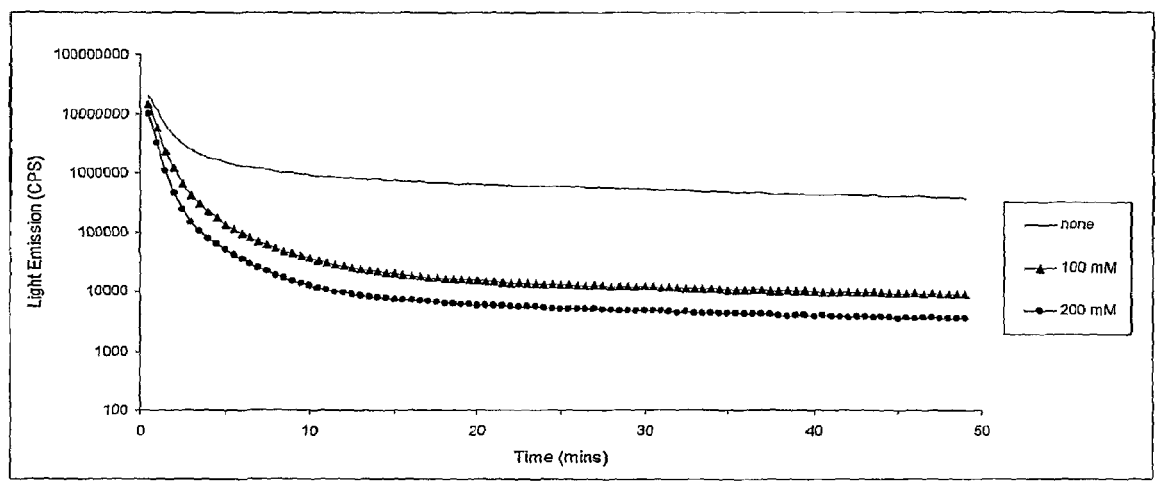

Experiments were performed as described in Example 5 for the non-secreted *Gaussia* and *Metridia* luciferases, except that the reducing agents used were: dithioerythritol (DTE) (FIGS. 6A and 6D); sodium sulfite (FIG. 6B); cysteamine (FIGS. 6C and 6E); TCEP (FIG. 6F); and β-mercaptoethanol (FIG. 6G). The data (FIGS. 6A to 6G) indicate that, as with DTT, other reducing agents also provide a rapid decline in light emission from *Gaussia* and *Metridia* luciferases.

Example 7

Figure 7:
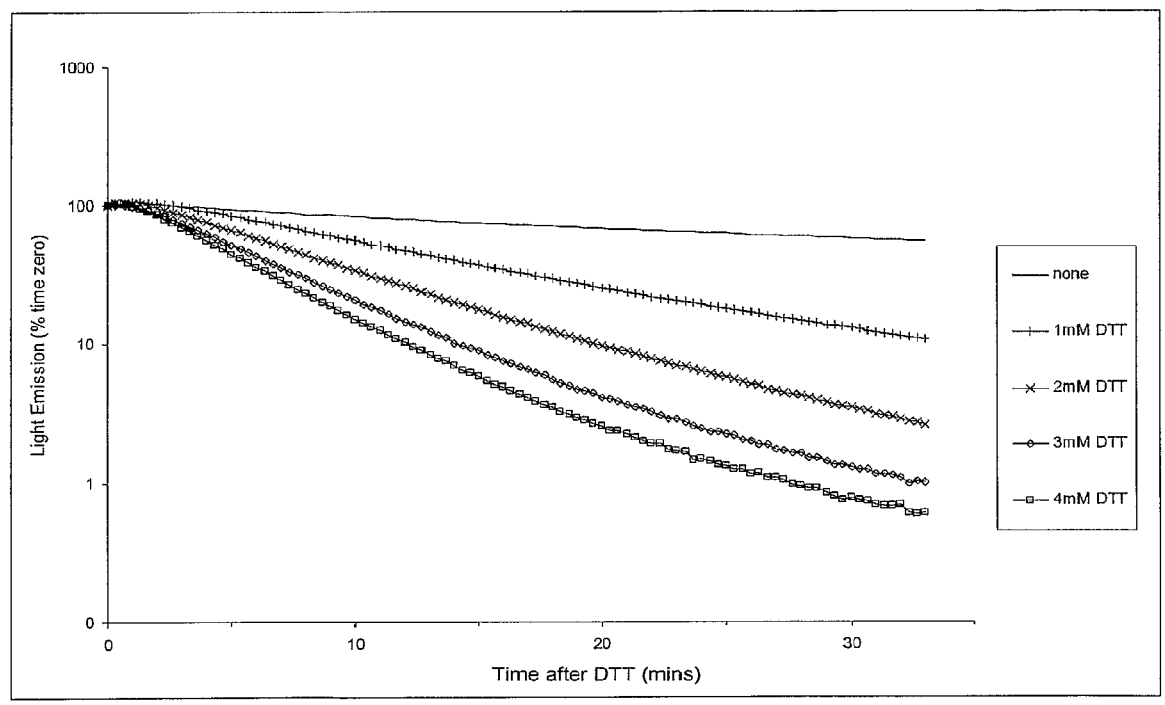
FIG. 7 shows the effect of DTT on the bioluminescent signal from non-secreted *Gaussia* luciferase when DTT is added during the glow phase of a previously initiated reaction.

Cell lysates comprising non-secreted *Gaussia* luciferase were prepared as described in Example 1. 60 ul of assay buffer comprising 25 mM Tris pH 7.75; 1 mM EDTA; 2 mM Ascorbic acid and 26 uM coelenterazine was added to 20 ul aliquots of lysate and left to incubate at room temperature for 40 minutes, such that the reaction entered its glow phase. After 40 minutes (time zero) a further 60 ul of assay buffer was added. This assay buffer was the same as the initial assay buffer except that it contained the indicated concentration of DTT and no coelenterazine. The light emission was measured in a time course following injection of the second assay buffer and expressed as a percentage of the light units at time zero (FIG. 7).

The data show that when DTT is added during the glow phase of a previously initiated reaction the same desirable rapid decline in light emission is observed as when reducing agents are added at the point of initiation of the reaction. This demonstrates that non-secreted *Gaussia* luciferase activity can be measured in a standard reaction such as a glow reaction and then subsequently terminated by addition of reducing agent. Alternatively, luciferase activity can be measured immediately after addition of the reducing agent; i.e. in a manner equivalent to its use in flash reactions. The lack of any significant decay in light emission during the first few seconds after injection of the reducing agent demonstrates that such a protocol would not cause any decrease in signal strength.

Part II: Reducing Agents can be Used to Conduct Multi-Reporter Assays Using Different Luciferases With Different Substrates Example 8

Figure 8:
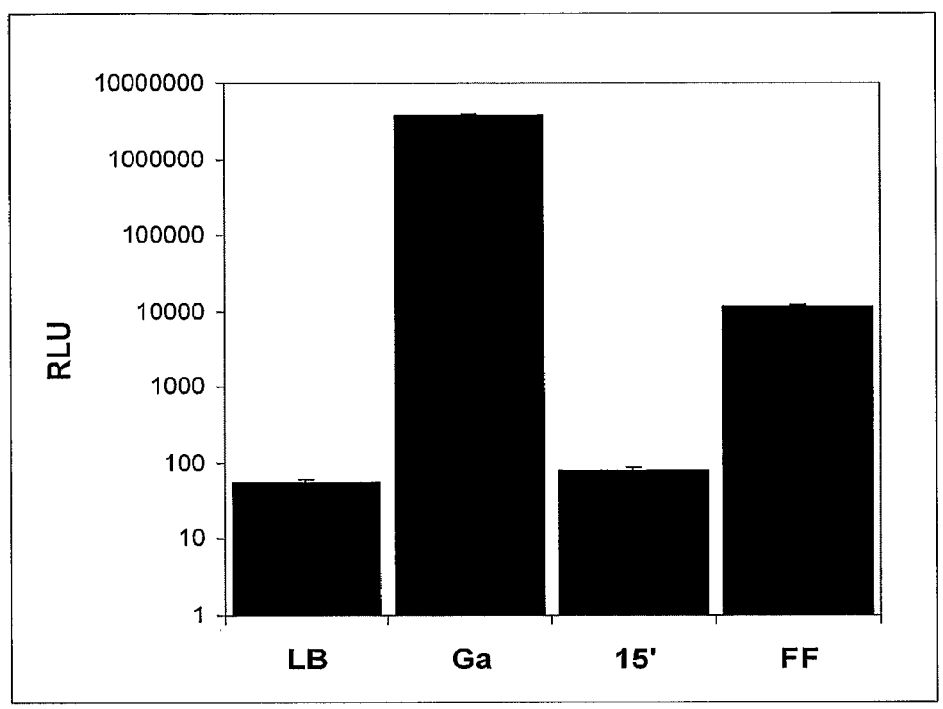
FIG. 8 shows bioluminescence (RLU) from a dual-luciferase assay in cells expressing a non-secreted *Gaussia* luciferase and a firefly luciferase. LB=signal measured immediately before addition of *Gaussia* luciferase assay buffer; Ga=signal measured immediately after addition of *Gaussia* luciferase assay buffer; 15'=signal measured 15 minutes after addition of *Gaussia* luciferase assay buffer (just prior to addition of firefly assay buffer); FF=signal measured 1 second after addition of firefly luciferase assay buffer.

HeLa cells stably expressing both a non-secreted and destabilized *Gaussia* luciferase and a destabilized firefly luciferase were plated onto 96-well plates and incubated overnight. Medium was removed and the cells lysed in 20 ul of the lysis buffer described in Example 1. Light emission was measured for 1 sec in a luminometer at the following times: immediately before addition of assay buffer (LB=background signal in absence of substrate); immediately after addition of *Gaussia* assay buffer (Ga) comprising 25 mM Tris pH 8.1; 1 mM EDTA, 2 mM Ascorbate, 23.6 uM Cz and 50 mM DTT; 15 mins after addition of Ga assay buffer (15 mins); and subsequently at 1 sec after addition of 60 ul of a firefly assay buffer (FF) comprising 25 mM Tris pH 7.35, 6 mM MgSO$_4$, 36 mM DTT, 0.11 mM EDTA, 0.58 mM ATP, 0.3 mM CoA, 0.52 mM Luciferin, 1 mg/ml BSA. The results shown in FIG. 8 illustrate a strong *Gaussia* luciferase bioluminescent signal that can be measured in a flash reaction but which decays to background levels within approximately 15 mins without intervention or the need to add quenching reagents. Subsequent addition of a firefly reagent allows measurement of the firefly signal, thus completing a dual-luciferase assay.

Example 9

293T cells were transiently transfected with either or both of a plasmid containing a destabilized firefly luciferase under the control of multiple tandem CRE (CRE-FF) or a destabilized, intracellular *Gaussia* luciferase driven by multiple tandem NFkB-binding sites (NFkB-Ga). Transfected cells were plated onto 96-well plates and incubated overnight. Quadruplicate wells were treated with 10 uM (final concentration) forskolin or 10 ng/ml TNF-alpha (TNF) or left untreated (control). Four hours later, the medium was removed and the luminescence from each luciferase was measured using the protocol described in Example 8.

Figure 9A:
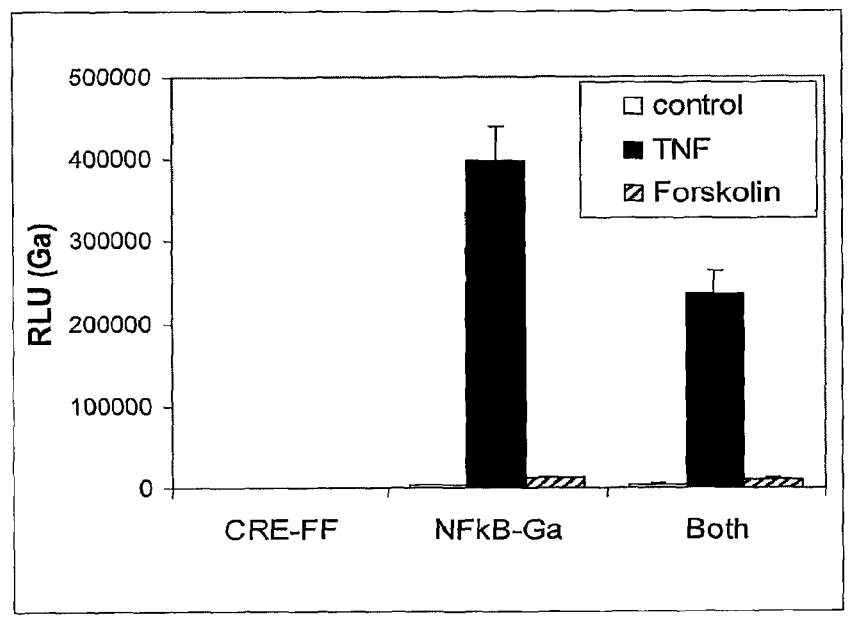
FIGS. 9A-B show luciferase activity (RLU) from cells expressing either a destabilized firefly luciferase under the control of cyclic AMP responsive element (CRE-FF) or a destabilized, intracellular *Gaussia* luciferase driven by multiple tandem NFkB-binding sites (NFkB-Ga) or both, in the presence of tumour necrosis factor (TNF) or forskolin. (A) Luciferase activity in the presence of *Gaussia* assay buffer. (B) Luciferase activity in the presence of firefly assay buffer.
Figure 9B:
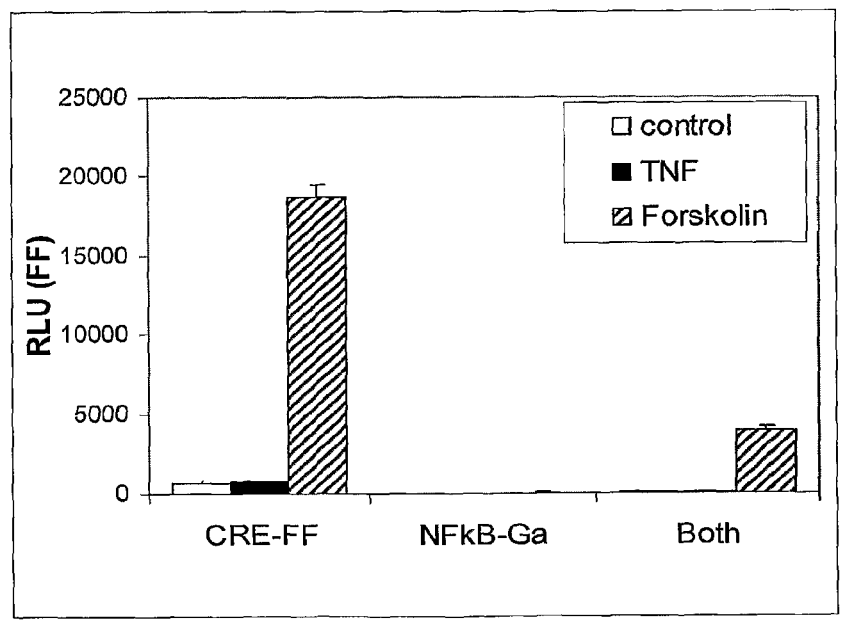

FIG. 9A shows the luminescent signal after addition of *Gaussia* assay buffer (see Example 5) and FIG. 9B shows the signal after addition of firefly assay buffer. It is evident from the results that the firefly luciferase gives essentially no luminescent signal in the *Gaussia* assay buffer (see FIG. 9A) and the *Gaussia* luciferase gives essentially no signal in the firefly assay buffer (see FIG. 9B). Thus, the dual-luciferase method is extremely effective at separating the two signals.

NFkB elements are known to respond strongly to TNF but not forskolin and the CRE respond strongly to forskolin but not TNF. As expected, therefore, NFkB-Ga (alone) was induced strongly by TNF but not forskolin (FIG. 9A), whereas CRE-FF (alone) was induced strongly by forskolin but not TNF (FIG. 9B). Importantly, the same result was seen in cells co-transfected with both constructs, demonstrating the success and validity of the dual-luciferase assay.

Part III: Reducing Agents can be Used to Conduct a Multi-Reporter Assay Using Different Luciferases With the Same Substrate Example 10

Flasks of HeLa cells were transiently transfected with expression plasmids encoding either non-secreted *Gaussia* luciferase or standard intracellular *Renilla* luciferase. 24 hours later, separate stock lysates were prepared from each flask and also from a control flask of non-transfected HeLa cells using the lysis buffer described in Example 1. Lysates were loaded onto a 96-well plate in quadruplicate as either 10 ul *Gaussia* luciferase plus 10 ul non-transfected (Ga), 10 ul *Renilla* luciferase plus 10 ul non-transfected (Rn) or 10 ul *Gaussia* luciferase plus 10 ul *Renilla* luciferase (Ga&Rn). Luciferase activity was measured immediately after addition of the assay buffer described in Example 8 and then measured again 1200 seconds later.

Figure 10A:
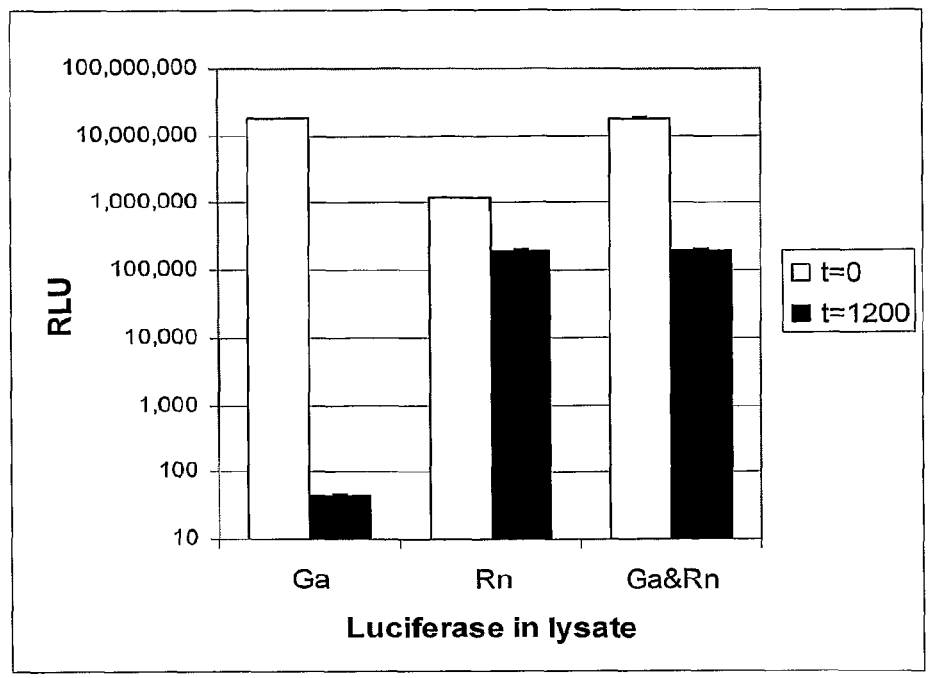
FIG. 10A shows luciferase activity (RLU) in cell lysates containing a non-secreted *Gaussia* luciferase (Ga), *Renilla* luciferase (Rn) or both luciferases in a mixed lysate (Ga&Rn) at 0 seconds (t=0) and 1200 seconds (t=1200).

FIG. 10A shows the raw data, expressed as relative light units (RLU). As expected, the *Gaussia* luminescent signal was initially very strong but decayed to background levels before the second read, whereas the *Renilla* luciferase generated showed a lower initial signal that decayed far less between the two reads. The mixed lysate (Ga&Rn) showed an intermediate level of decay.

Since the *Gaussia* luciferase no longer contributes to the detectable relative light units (RLU) at the second read, this reading is an accurate measure of *Renilla* luciferase and can be used to compare levels of *Renilla* luciferase between samples. The initial read is a combination of signals from both *Gaussia* and *Renilla* luciferases. However, the signal generated by *Gaussia* luciferase can be determined by subtracting the initial *Renilla* luciferase signal from the combined, measured signal at time-zero. To determine the initial *Renilla* luciferase signal, the *Renilla*-only (Rn) lysate was used as a standard to calculate the rate of decay in light emission from *Renilla* luciferase. Specifically, the decay constant "k" was calculated where k=(initial Rn signal)/(Rn signal at 1200 secs). The initial Rn signal was then calculated as (Rn signal at 1200 secs)×k and the initial *Gaussia* luciferase signal was calculated by subtracting that value from the initial combined (Ga&Rn) signal.

Figure 10B:
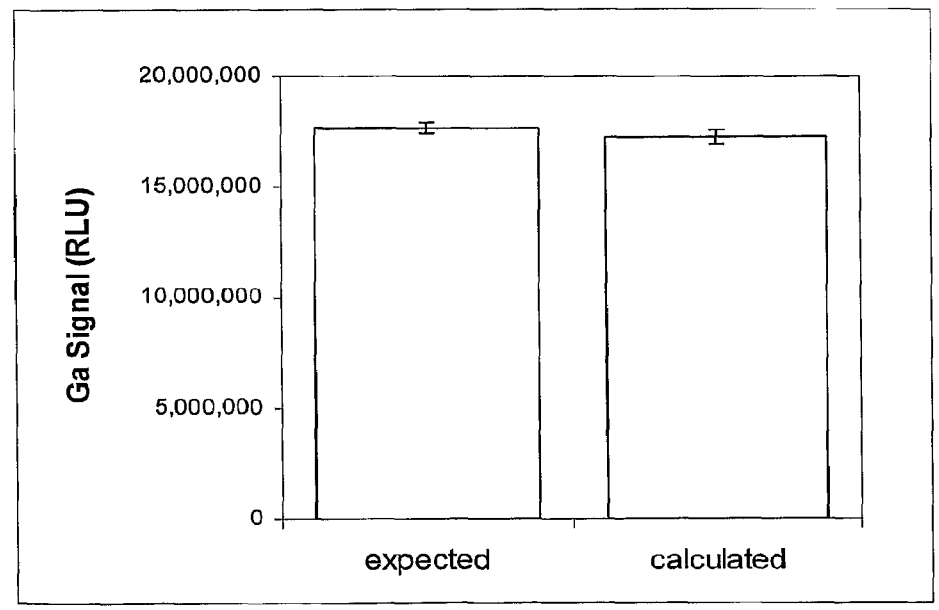
FIG. 10B shows a comparison of measured (calculated) and expected activity for the non-secreted *Gaussia* luciferase from FIG. 10A, determined as described in Example 10.

FIG. 10B compares these calculated values of *Gaussia* luciferase activity in the combined samples (calculated) to the actual values of *Gaussia* luciferase activity measured in samples containing the same amount of *Gaussia* luciferase but without any *Renilla* luciferase present (expected; i.e. (Ga) in FIG. 10A). The difference between measured (expected) and calculated values was very small and not statistically significant, demonstrating that it is possible to perform a dual-luciferase assay comprising a single assay buffer, even when there is no difference between the luciferases in terms of the substrate type or wavelength of light emission. Unlike other dual-luciferase assays previously described, which rely on the use of quenching reagents or luciferases with different emission wavelengths, the method described herein, utilizes differences between the luciferases in terms of the kinetics of light emission. To the inventors' knowledge, the use of temporal differences in light emission to distinguish different luciferase signals has not previously been reported. The separation of the two signals was greatly enhanced in the current example by including a reducing agent such as DTT. This was made possible based on the surprising finding that whereas DTT stabilizes the signal from intracellular luciferases such as *Renilla* and firefly luciferases, it dramatically shortens the duration of light emission from luciferases that are normally secreted in their wild-type state, such as *Gaussia* luciferase.

Example 11

The inventors contemplated the possibility of a dual luciferase assay based on the use of one secreted and one intracellular luciferase. Cells expressing both luciferases can be used as a source of both conditioned medium (comprising the secreted luciferase) and cellular lysate (comprising the intracellular luciferase). In this manner, the 2 luciferases are separated by their location rather than differences in substrate specificity. However, such an assay would require that the lysate is free of detectable secreted luciferase and this seemed unlikely considering that secreted luciferases are produced intracellularly and must travel through the endoplasmic reticulum (ER) prior to secretion. Indeed preliminary experiments revealed that cells expressing secreted *Gaussia* luciferase contain large amounts of the luciferase, even after removal of the culture medium and repeated washing of the cells. Clearly, at least a portion of the resulting lysate signal is derived from recently translated luciferase molecules that have not yet traversed the ER and been secreted. Potentially, some of this signal may also derive from older luciferase molecules that have either become stuck inside the ER or have been secreted but have become bound to the extracellular side of the cell membrane. Regardless of the source of this interfering luciferase signal, the inventors reasoned that it could be eliminated by including reducing agent in the lysis buffer.

To test this hypothesis, HeLa cells were co-transfected with plasmids TRE-Rn and CMV-Ga (wild type, secreted), either alone or in combination. The latter provides constitutive expression of secreted *Gaussia* luciferase, whilst the former provides a doxycycline-repressible expression of intracellular *Renilla* luciferase. The cells were incubated overnight, the medium was removed and the cells rinsed once before addition of a fresh aliquot of medium either with or without 2 ug/ml doxycyline. At 2, 6 and 24 hrs later, samples of conditioned medium were taken. The cells were rinsed in fresh medium before being lysed using lysis buffer comprising 25 mM Tris pH 8.1, 150 mM NaBr, 1 mM EDTA, 63.4 uM sodium oxalate, 0.1% NP40 substitute, 5% glycerol; either with or without 50 mM DTT. 20 ul aliquots of conditioned medium and cell lysate were then assayed for luciferase activity following addition of 60 ul of assay buffer comprising 25 mM Tris pH 7.75; 1 mM EDTA; 2 mM Ascorbic acid and 26 uM coelenterazine.

Figure 11A:
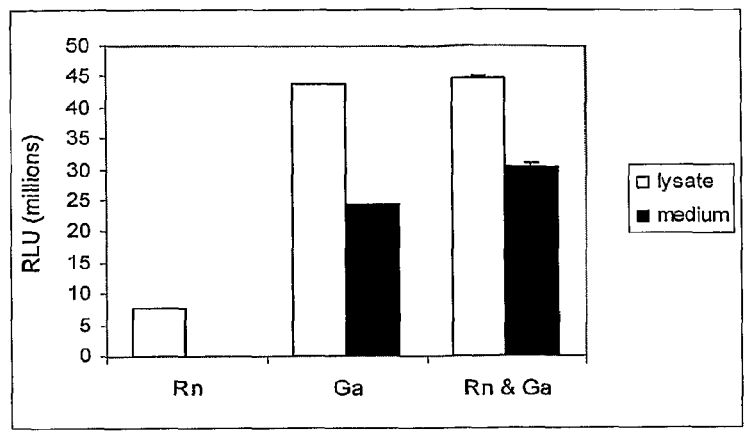
FIGS. 11A-D show luciferase activity (RLU) in the conditioned medium and cell lysate of cells expressing CMV-driven *Gaussia* luciferase (Ga or CMV-*Gaussia*) and a TRE-driven non-secreted *Renilla* luciferase (Rn or TRE-*Renilla*). (A and C) using lysis buffer without DTT, (B and D) using lysis buffer containing DTT.
Figure 11B:
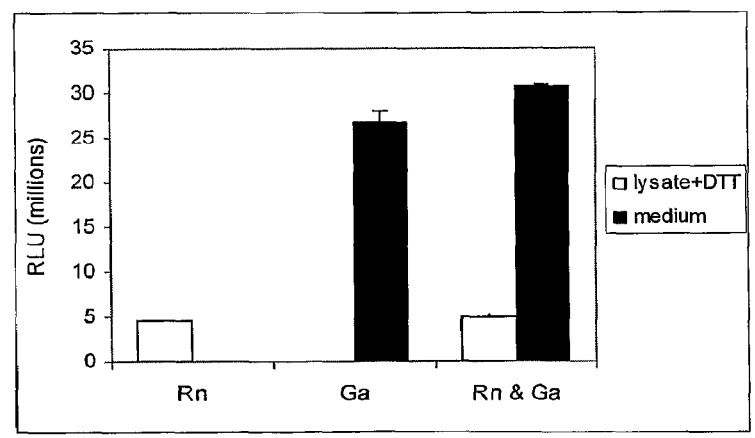

FIGS. 11A and 11B show data from samples without doxycycline at the 2 hour time-point. Using standard lysis buffer (FIG. 11A), a strong signal was detected in the lysate of cells expressing only the secreted *Gaussia* (Ga) luciferase. Indeed, this signal was even higher than in lysates of cells expressing only the non-secreted *Renilla* (Rn) luciferase. Clearly, the secreted *Gaussia* luciferase is not confined to the conditioned medium. In contrast, when DTT was included in the lysis buffer (FIG. 11B), no signal was detected in the lysate of cells expressing only *Gaussia* luciferase. With this protocol it is therefore possible to distinguish the non-secreted *Renilla* luciferase from the secreted *Gaussia* luciferase, as evidenced by the lysate-only signal with *Renilla* and the medium-only signal with *Gaussia*.

Figure 11C:
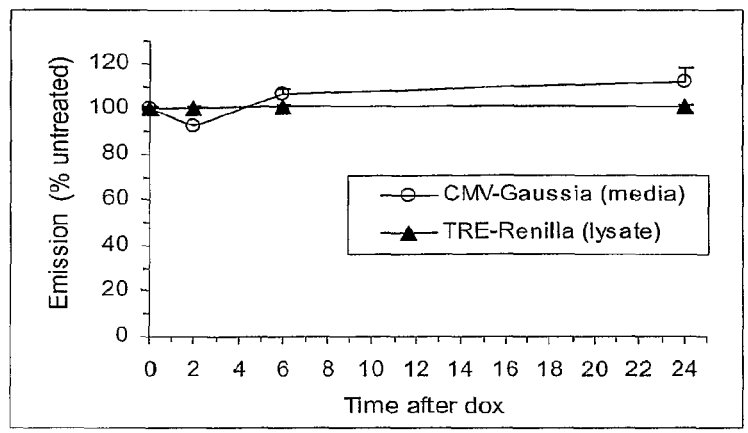
Figure 11D:
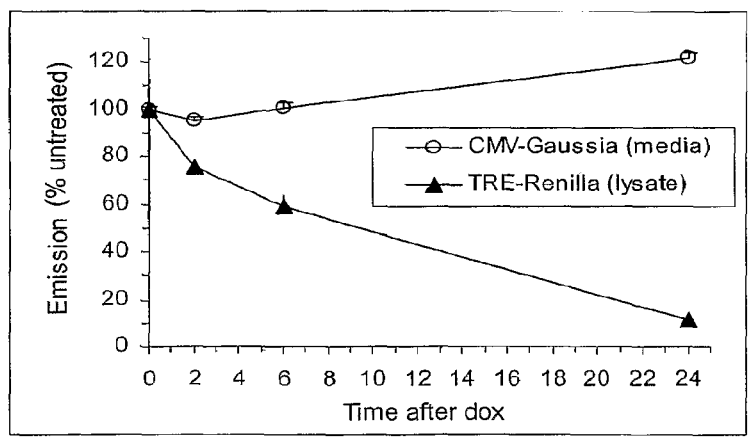

To further demonstrate the functionality and utility of this system, data from all time-points was expressed as +doxycycline relative to −doxycycline (FIGS. 11C and 11D). It should be noted that the *Renilla* luciferase was linked to a TRE promoter such that only the *Renilla* luciferase would decrease over time. Thus a system that correctly distinguishes between the secreted *Gaussia* (Ga) luciferase and the non-secreted *Renilla* (Rn) luciferase should show a decline in the cell lysate values but not the conditioned medium values. This effect is indeed evident in FIG. 11D, which represents the data obtained using lysis buffer with DTT. In contrast, using lysis buffer without DTT (FIG. 11C) it is clearly not possible to separate the signals of the two luciferases.

Part IV: Reducing Agents Provide Lower Background Signals

Example 12

Non-transfected HeLa cells and HeLa cells expressing non-secreted *Gaussia* luciferase were subjected to luciferase assays as follows. Cells were plated in equal aliquots onto a 96-well plate and incubated overnight. Medium was removed and cells lysed in 20 ul of the lysis buffer described in Example 1. Forty minutes later, light emission was measured using a Wallac Victor 3 luminometer (Perkin Elmer) immediately before and after injection of 60 ul of assay buffer comprised 25 mM Tris pH 8.1, 23.6 uM coelenterazine, 1 mM EDTA, 2 mM ascorbate plus the indicated concentration of DTT (see FIG. 8).

Figure 12A:
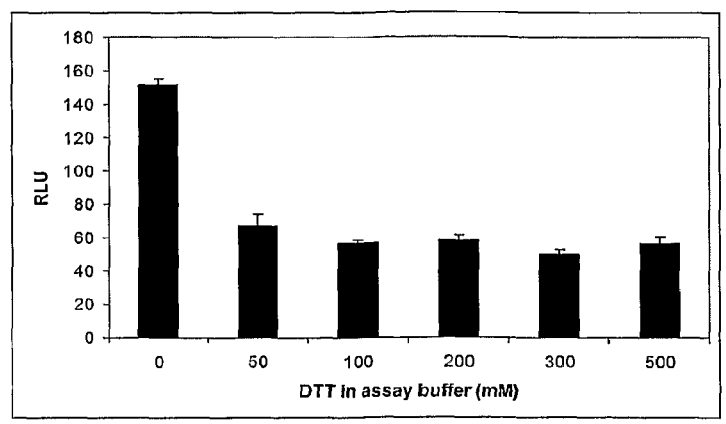
FIGS. 12A-C show the effect of varying concentrations of DTT on background luminescent signal (A) and (B) and flash intensity (C) from a non-secreted *Gaussia* luciferase.
Figure 12B:
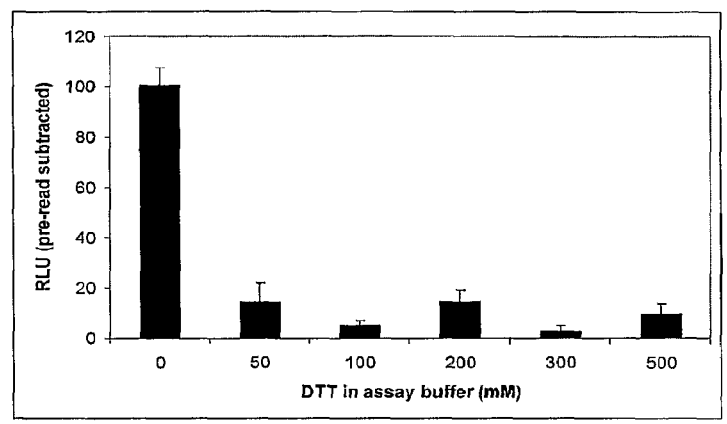

FIG. 12A shows raw data expressed as relative light units (RLU) after injection. Since no luciferase was present in the cell lysates, these data represent the background signal of the assay. FIG. 12B shows the data after subtraction of the pre-read (measurement before addition of assay buffer). Thus, these data represent the background signal generated by the assay buffer. These data show that inclusion of DTT in the assay buffer provides a reduction of more than 50% in the overall background signal (FIG. 12A) and a reduction of more than 80% in the background signal generated by the assay buffer (FIG. 12B).

Figure 12C:
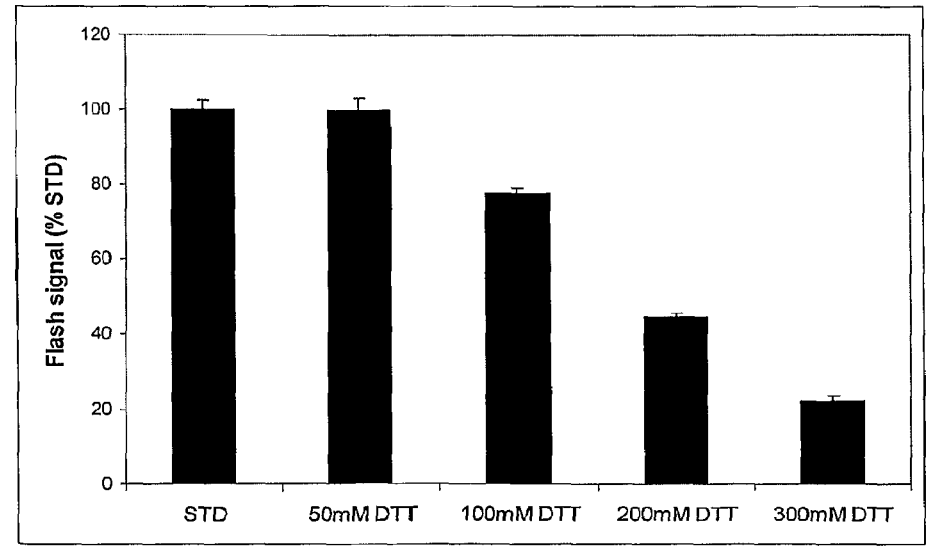

FIG. 12C shows that 50 mM DTT does not reduce the true luciferase signal generated in flash reactions with HeLa cell lysate containing non-secreted *Gaussia* luciferase. Thus, the inclusion of 50 mM DTT in the assay buffer reduces background signal (FIGS. 12A & 12B) and markedly shortens the kinetics of light emission (see other examples) but does not compromise the intensity of the true flash signal from *Gaussia* luciferase.

Part V: Reducing Agents Prevent or Limit the Decline in Assay Buffer Activity

Example 13

Figure 13:
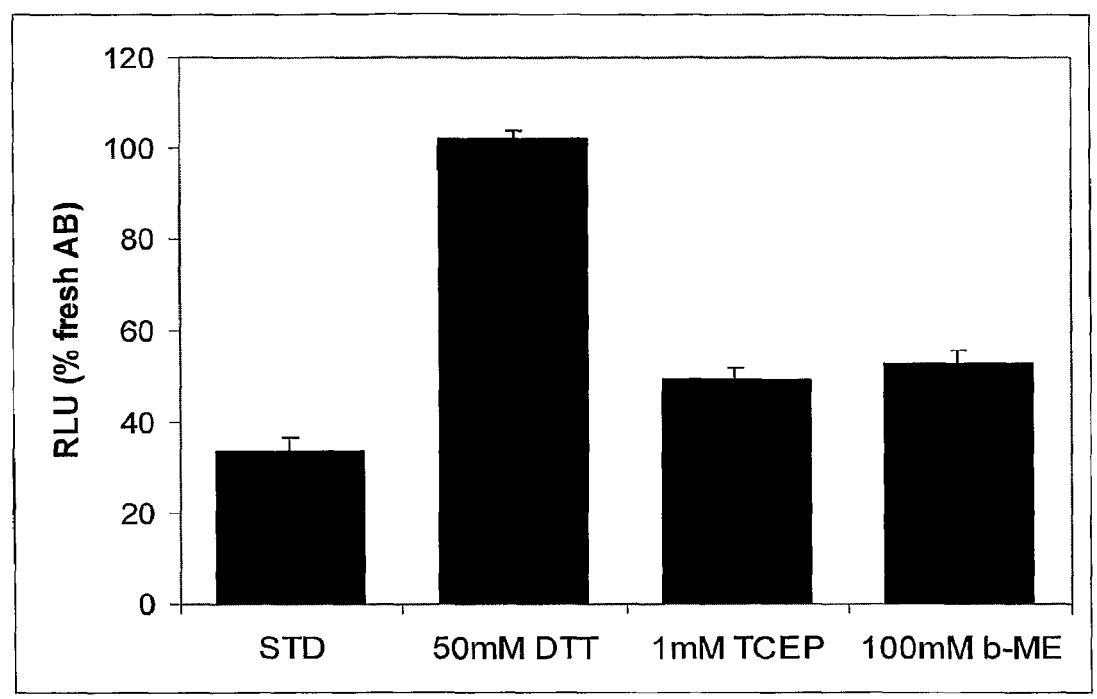
FIG. 13 shows bioluminescent signal intensity (RLU) generated from non-secreted *Gaussia* luciferase in 22 h old assay buffer as a percentage of the signal intensity in fresh assay buffer, in the presence or absence of reducing agents DTT, TCEP or β-mercaptoethanol (b-ME).

A stock lysate of *Gaussia* luciferase was prepared by lysing a flask of HeLa cells stably expressing non-secreted *Gaussia* luciferase with the lysis buffer described in Example 1. 20 ul of lysate was loaded onto each well of a 96 well plate and light emission was measured in flash reactions following injection of either standard assay buffer as described in Example 1 (STD) or the same assay buffer further comprising the amount and type of reducing agent as shown in FIG. 13. Quadruplicate samples were measured for each group using freshly prepared assay buffer. The assay buffers were then stored in the dark at 4° C. for 22 hrs and the protocol repeated.

FIG. 13 shows the signal intensity using this aged assay buffer as a percentage of the signal intensity obtained from the same assay buffer when it was fresh. In the absence of reducing agent the activity of the assay buffer (STD) declined by more than 60% during storage. All reducing agents were effective at reducing this decline and of particular note, the presence of 50 mM DTT completely abolished all evidence of assay buffer degradation.

Example 14

Figure 14:
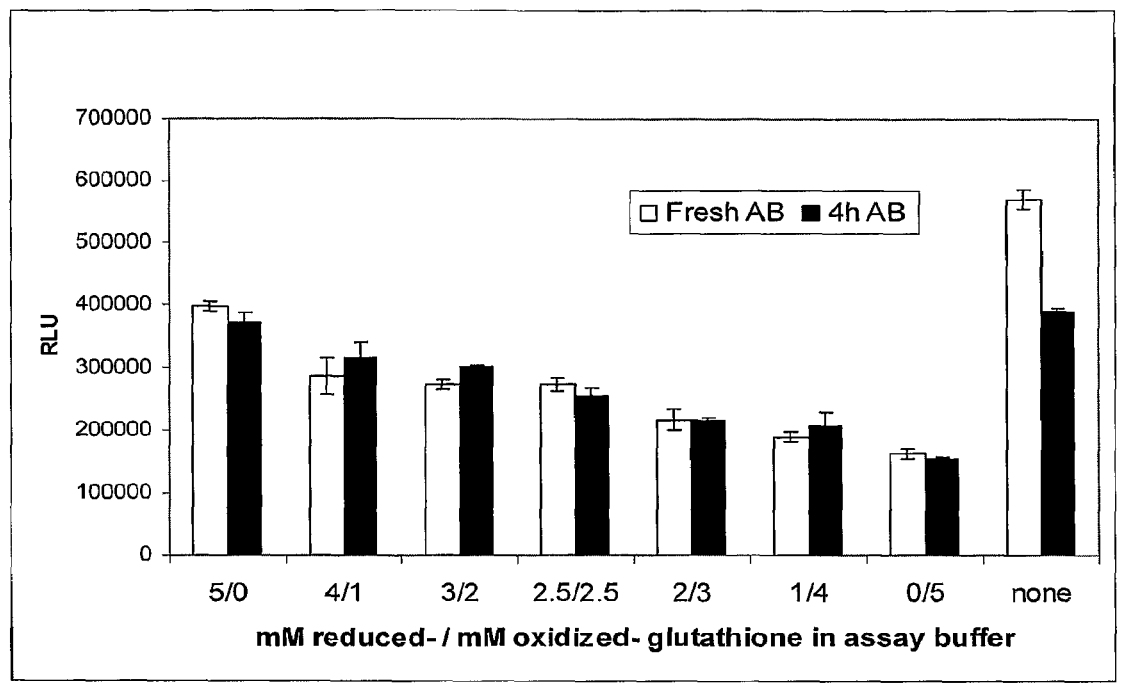
FIG. 14 shows luminescence (RLU) in cell lysates of a non-secreted *Gaussia* luciferase in fresh assay buffer (AB) and assay buffer stored for 4 hours prior to use (4 h AB), in the presence of varying ratios of oxidised:reduced glutathione.

HeLa cells expressing a destabilised, non-secreted *Gaussia* luciferase were plated in equal aliquots onto 96-well plates and incubated overnight. The same lysis buffer was used for all samples. Luciferase activity was measured using fresh assay buffer containing the amounts and ratio of reduced and oxidised glutathione indicated in FIG. 14. The assay buffers were then stored at room temperature for 4 hrs and used again to measure replicate samples. FIG. 14 shows that in the absence of glutathione, the activity of the assay buffer declined by about 32%. This decline was completely blocked by the presence of 5 mM glutathione, including reduced glutathione alone, oxidised glutathione alone and each ratio of the two combined. The baseline activity of the fresh buffers, however, showed that glutathione, and particularly oxidised glutathione, reduces the assay buffer activity, albeit with the advantageous effect of providing stability.

Example 15

Figure 15:
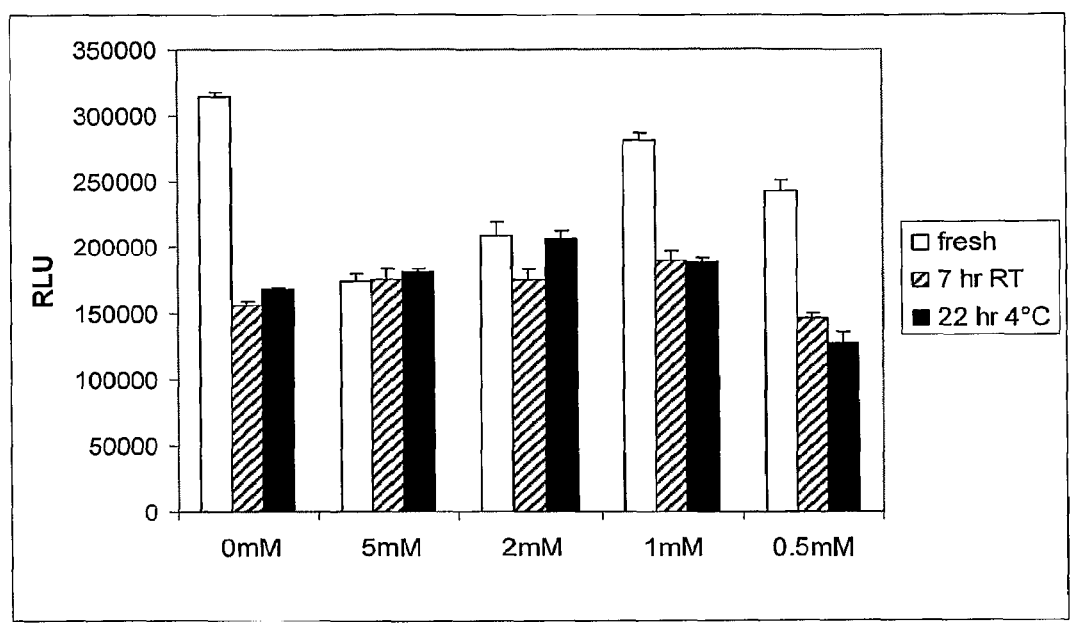
FIG. 15 shows shows activity (RLU) in cell lysates of a non-secreted *Gaussia* luciferase in fresh assay buffer, assay buffer stored at room temperature (RT) for 7 hours prior to use or assay buffer stored at 4° C. for 22 hours prior to use, in the presence of varying concentrations of a 3:2 ratio of reduced:oxidised glutathione.

HeLa cells expressing a destabilised, non-secreted *Gaussia* luciferase were plated in equal aliquots onto 96-well plates and incubated overnight. The same lysis buffer was used for all samples. Luciferase activity was measured using fresh assay buffer containing the total amounts of glutathione (3:2 ratio of reduced:oxidized) indicated in FIG. 15. The assay buffers were then stored at room temperature for 7 hrs or at 4° C. for 22 hrs and used again to measure replicate samples. FIG. 15 shows that in the absence of glutathione, the activity of the assay buffer declined by about 50%. This decline was completely blocked by the presence of 5 mM glutathione, although initial activity was reduced in this buffer. Lower amounts of glutathione showed an intermediate effect in terms of both protection from loss of activity over time and level of initial reduction in activity.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

What is claimed is:

1. A method for determining the amount or activity of at least one luciferase in a sample that comprises a recombinant luciferase that, in its wild type form, is a secreted luciferase, the method comprising:
    (i) contacting the sample with a composition comprising a reducing agent,
    (ii) contacting the sample with a composition comprising a luciferase substrate, and
    (iii) detecting bioluminescence in the sample.

2. The method of claim 1, wherein the recombinant luciferase is a non-secreted derivative of a luciferase that is secreted in its native form.

3. The method of claim 1, wherein the luciferase substrate is a coelenterazine.

4. The method of claim 1, wherein the recombinant luciferase is from *Gaussia* spp., *Pleuromamma* spp., *Metridia* spp., *Cypridina* spp., or *Oplophorus* spp., or is a modified form thereof, where the modification is i) a deletion of the signal sequence, ii) fusion to a second, intracellular polypeptide, iii) fusion or conjugation to a second polypeptide that comprises a selectable marker, and/or iv) introduction of one or more destabilizing elements selected from a PEST sequence, a degron, and ubiquitin.

5. The method of claim 1, wherein the reducing agent is selected from the group consisting of dithiothreitol (DTT), β-mercaptoethanol, reduced glutathione, and tris(2-carboxyethyl)phosphine (TCEP).

6. The method of claim 1, wherein the reducing agent comprises a thiol group.

7. The method of claim 1, wherein the sample is contacted with a composition comprising both the reducing agent and the luciferase substrate.

8. The method of claim 1, wherein the sample is used directly or wherein the sample is subjected to a pre-treatment.

9. The method of claim 8, wherein the pre-treatment comprises a cell lysis step.

10. The method of claim 1, further comprising adding an additional composition to the sample and detecting bioluminescence in the sample, wherein the additional composition comprises a substrate of an additional luciferase in the sample.

11. The method of claim 10, wherein the additional luciferase is derived from a *Coleoptera* species or a *Diptera* species.

12. The method of claim 10, wherein the additional luciferase utilizes luciferin as a substrate.

* * * * *